United States Patent [19]

Schaaf et al.

[11] 3,984,424
[45] Oct. 5, 1976

[54] P-BIPHENYL ESTERS OF 15-SUBSTITUTED-ω-PENTANORPROSTAGLANDINS

[75] Inventors: Thomas K. Schaaf, Old Lyme; Jasjit S. Bindra, Groton; Michael R. Johnson, Gales Ferry, all of Conn.

[73] Assignee: Pfizer Inc., New York, N.Y.

[22] Filed: July 3, 1974

[21] Appl. No.: 485,508

Related U.S. Application Data

[63] Continuation-in-part of Ser. No. 304,815, Nov. 7, 1972, abandoned, and a continuation-in-part of Ser. No. 428,672, Dec. 27, 1973, abandoned.

[52] U.S. Cl. ...................... 260/332.2 A; 260/340.5; 260/347.4; 260/468 D; 260/473 R; 260/514 D; 260/520 B
[51] Int. Cl.$^2$ ........................................ C07D 333/24
[58] Field of Search ................ 260/468 D, 332.2 A, 260/473 R, 340.5, 347.4

[56] References Cited
FOREIGN PATENTS OR APPLICATIONS
2,155,546  5/1972  Germany ..................... 260/468 D

*Primary Examiner*—Lewis Gotts
*Assistant Examiner*—Cary Owens
*Attorney, Agent, or Firm*—Connolly and Hutz

[57] ABSTRACT

The p-biphenyl esters of 15-substituted-ω-pentanorprostaglandins are disclosed. The novel prostaglandin esters of the invention exhibit the biological properties of corresponding prostaglandins from which they are derived, but have reduced side effects, and are further valuable because they are easily crystallized and thus may be simply isolated and purified and compounded into medicaments.

37 Claims, No Drawings

P-BIPHENYL ESTERS OF 15-SUBSTITUTED-ω-PENTANORPROSTAGLANDINS

CROSS REFERENCE TO RELATED APPLICATIONS

This application is a continuation-in-part of our earlier filed applications, Ser. No. 304,815 filed Nov. 7, 1972, and now abandoned, and Ser. No. 428,672, filed Dec. 27, 1973 and now abandoned.

BACKGROUND OF THE INVENTION

This invention relates to certain novel analogs of the naturally occurring prostaglandins. In particular, it relates to novel 15-substituted-ω-pentanorprostaglandins and various novel intermediates useful in their preparation.

The prostaglandins are C-20 unsaturated fatty acids which exhibit diverse physiological effects. For instance, the prostaglandins of the E and A series are potent vasodilators (Bergstrom et al., *Acta Physiol. Scand.* 64:332-33 1965 and Bergstrom et al., *Life Sci.* 6:449-455, 1967) and lower systemic arterial blood pressure (vasodepression) on intravenous administration (Weeks and King, *Federation Proc.* 23:327, 1964; Bergstrom, et al., 1965 op. cit.; Carlson, et al., *Acta Physiol. Scand.* 75:161-169, 1969). Another well known physiological action for $PGE_1$ and $PGE_2$ is bronchodilation (Cuthbert, *Brit. Med. J.* 4:723-726, 1969).

Still another important physiological role for the natural prostaglandins is in connection with the reproductive cycle. $PGE_2$ is known to possess the ability to induce labor (Karim, et al., *J. Obstet Gynaec. Brit. Cwlth.* 77:200-210, 1970), to induce therapeutic abortion (Bygdeman, et al., *Contraception*, 4, 293 (1971) and to be useful for control of fertility (Karim, *Contraception* 3, 173 (1971). Patents have been obtained for several prostaglandins of the E and F series as inducers of labor in mammals (Belgian Patent 754,158 and West German Patent 2,034,641), and on the use of $PGF_1$, $F_2$, and $F_3$ for control of the reproductive cycle (South African Patent 69/6089). It has been shown that luteolysis can take place as a result of administration of $PGF_{2\alpha}$ [Labhsetwar, Nature 230 528 (1971)] and hence prostaglandins have utility for fertility control by a process in which smooth muscle stimulation is not necessary.

Still other known physiological activities for $PGE_1$ are in the inhibition of gastric acid secretion (Shaw and Ramwell, In: *Worcester Symp. on Prostaglandins*, New York, Wiley, 1968, p.55-64) and also of platelet aggregation (Emmons, et al., *Brit. Med. J.* 2:468-472, 1967).

It is now known that such physiological effects will be produced in vivo for only a short period, following the administration of a prostaglandin. A substantial body of evidence indicates that the reason for this rapid cessation of activity is that the natural prostaglandins are quickly and efficiently metabolically deactivated by β-oxidation of the carboxylic acid side-chain and by oxidation of the 15α-hydroxyl group (Anggard, et al., *Acta. Physiol. Scand.*, 81, 396 (1971) and references cited therein). It has been shown that placing a 15-alkyl group in the prostaglandins has the effect of increasing the duration of action possibly by preventing the oxidation of the C15-hydroxyl [Yankee and Bundy, JACS 94, 3651 (1972) Kirton and Forbes, *Prostaglandins*, 1, 319 (1972)].

It was, of course, considered desirable to create analogs of the prostaglandins which would have physiological activities equivalent to the natural compounds, but in which the selectivity of action and the duration of the activity would be increased. Increased selectivity of action would be expected to alleviate the severe side effects, particularly gastrointestinal side effects, frequently observed following systemic administration of the natural prostaglandins (*Lancet*, 536, 1971).

Furthermore, it was considered necessary to produce compounds which could be readily crystallized since the isolation and purification of non-crystalline products is tedious and inefficient.

SUMMARY OF THE INVENTION

These needs are met by the novel compounds of this invention in the parabiphenyl esters of ω-pentanorprostaglandins having at the $C_{15}$ position on hydrogen or lower alkyl group and one substituent (A) of the structure:

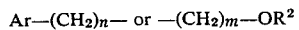

wherein
  $n$ is an integer from 0 to 5, with the proviso that when $n$ is zero, said prostaglandin is a 13,14 dihydroprostaglandin,
  $m$ is an integer from 2 to 3,
  $R^2$ is lower alkyl, and
  Ar is α- or β-furyl; α- or β-thienyl; α- or β-naphthyl; phenyl; 3,4-dimethoxyphenyl; 3,4-methylenedioxyphenyl; 3,4,5-trimethoxyphenyl or monosubstituted phenyl wherein said substituent is halo, trifluoromethyl, phenyl, lower alkyl or lower alkoxy.

Particularly preferred prostaglandin analogs of this invention have the structure:

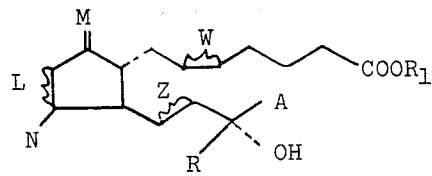

wherein A is:

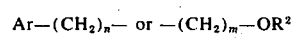

wherein
  $n$ is an integer from 0 to 5,
  $m$ is an integer from 2 to 3,
  $R^2$ is lower alkyl,
  Ar is α- or β-furyl; α- or β-thienyl; α- or β-naphthyl; phenyl; 3,4-dimethoxy phenyl; 3,4-methylenedioxyphenyl; 3,4,5-trimethoxyphenyl or monosubstituted phenyl wherein said substituent is halo, trifluoromethyl, phenyl, lower alkyl or lower alkoxy,
  $R_1$ is parabiphenyl;
  R is hydrogen or lower alkyl;
  W and L are each a single bond or cis double bond;
  Z is single bond or trans double bond; with the proviso that when $n$ is zero, Z is a single bond;
  M is keto,

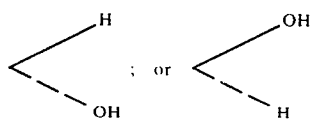

N is hydrogen or α-hydroxyl;
and wherein L, M and N are so selected as to complete the structure of a prostaglandin of the A, E or F series.

In addition to the p-biphenyl esters of said 15-substituted-ω-pentanorprostaglandins wherein the prostaglandin is $PGF_{1\alpha}$, $PGF_{1\beta}$, $PGE_1$, $PGA_1$; 13,14-dihydro $PGF_{1\alpha}$, $PGF_{1\beta}$, $PGE_1$, and $PGA_1$; $PGF_{2\alpha}$, $PGF_{2\beta}$, $PGE_2$, $PGA_2$; 13,14-dihydro $PGF_{2\alpha}$, $PGF_{2\beta}$, $PGE_2$, and $PGA_2$; and 15-lower alkyl derivatives of the above compounds, this invention further comprises useful intermediates for the synthesis of these prostaglandins as follows:

a compound of the structure:

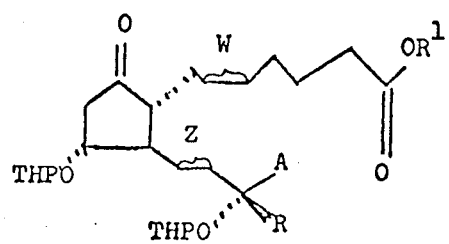

and a compound of the structure:

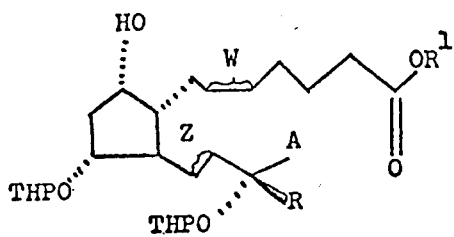

wherein A, R, Z, W, THP, and $R^1$ are as defined above.

Especially preferred compounds of this invention are para bi-phenyl esters of the following prostaglandins: 16-phenyl-ω-tetranor prostaglandin $E_2$, 13,14 dihydro 16-phenyl-ω-tetranor $PGE_2$, 16-phenyl-ω-tetranor $PGE_1$, 16-phenyl-ω-tetranor $PGE_0$, 17-phenyl-ω-tetranor $PGE_2$, 17-phenyl-ω-trisnor $PGF_{2\alpha}$, 17-α-furyl-ω-trisnor $PGF_{2\alpha}$, 16β-naphthyl-ω-tetranor $PGE_2$, 16o-tolyl-ω-tetranor $PGE_2$, 16p-tolyl-ω-tetranor $PGE_2$, 16-paramethoxyphenyl-ω-tetranor $PGE_2$, 16α-thienyl-ω-tetranor $PGE_2$, 16β-thienyl-ω-tetranor $PGE_2$, and other preferred compounds of this invention are the 15-phenyl 13,14-dihydro-ω-pentanor $PGE_2$, 15-methyl-16-phenyl-13,14-dihydro-ω-tetranor $PGE_2$, 19-oxa $PGE_2$, 19-oxa $PGF_{2\alpha}$, 20-oxa-ω-homo $PGE_2$, 17-oxa $PGF_{2\alpha}$, 13,14-dihydro 15-epi 16-phenyl-ω-tetranor $PGE_2$, 16-phenyl-ω-tetranor $PGF_{2\alpha}$, 13,14-dihydro 16-phenyl-ω-tetranor $PGF_{2\beta}$, 16-parabiphenyl-ω-tetranor $PGE_2$ and 15 epi 16β-naphthyl-ω-tetranor $PGE_2$, 20-oxa-ω-homo $PGF_{2\alpha}$ and 16α-thienyl-ω-tetranor $PGE_1$.

It will be understood that as herein used, the expression "prostaglandin of the 'zero' series," for example $PGE_0$, refers to prostaglandin in which the 5-6 and 13-14 double bonds have been saturated; i.e.: $PGE_0$ is 5-6, 13-14, tetrahydro $PGE_2$. In addition, the phrases "one series" or "two series" as herein employed refer to the degree of unsaturation in the side chains, e.g., $PGE_2$, $PGA_2$ and $PGF_{2\alpha}$, are prostaglandins of the "two series" whereas $PGE_1$, $PGF_{1\alpha}$ and $PGA_1$ are prostaglandins of the "one series". As used herein and in the claims, the term prostaglandin is understood to embrace both epimers at $C_{15}$. Furthermore as herein employed the phrase lower "alkyl group" refers to alkyl groups containing from 1 to 4 carbon atoms.

It will be understood by those skilled in the art that in structures depicting hemiacetals, no sterochemistry is implied at the lactol carbon.

DETAILED DESCRIPTION OF THE INVENTION

The invention will be better understood by referring first to reaction schemes A-E, which, in connection with the accompanying description, illustrate the synthesis of the ω-pentanorprostaglandins.

As shown in scheme A, the first step (1 → 2) is the condensation of the appropriate ester with a dialkyl methyl-phosphonate to produce ketophosphonate 2. Typically, the desired methyl ester is condensed with dimethyl methyl phosphonate.

In 2 → 3 the ketophosphonate 2 is caused to react with the known [Corey et al., J. Am. Chem. Soc., 93, 1491 (1971)]aldehyde H to produce the enone 3.

The enone 3 after chromatography or crystallization can be converted to a mixture of tertiary alchols 13 and 14 by reaction with the appropriate lithium alkyl and the isomeric 13 and 14 can be separated by column chromatography. The enone 3 can be reduced with zinc borohydride to a mixture of alcohols, 4 and 5 which can be separated as above. Isomer separation at this stage is not absolutely necessary and the epimeric mixture may be carried through subsequent steps to the final prostaglandin analogs which may then be separated. In this reaction ethers such as tetrahydrofuran or 1,2-dimethoxyethane are usually employed as solvents. Further transformations of 4 are shown on scheme B.:

4 → 6 is a base catalyzed transesterification in which the p-biphenyl-carbonyl protecting group is removed. This is most conveniently conducted with potassium carbonate in methanol or methanol-tetrahydrofuran solvent. 6 → 7 involves the protection of the two free hydroxyl groups with an acid-labile protecting group. Any sufficiently acid-labile group is satisfactory; however, the most usual one is tetrahydropyranyl, which can be incorporated in the molecule by treatment with dhydropyran and acid catalyst in an anhydrous medium. The catalyst is usually p-toluenesulfonic acid.

Scheme A
$$A-COOCH_3 \longrightarrow A-\underset{O}{\overset{\parallel}{C}}-CH_2-\underset{\uparrow O}{P}(OCH_3)_2$$
1   2
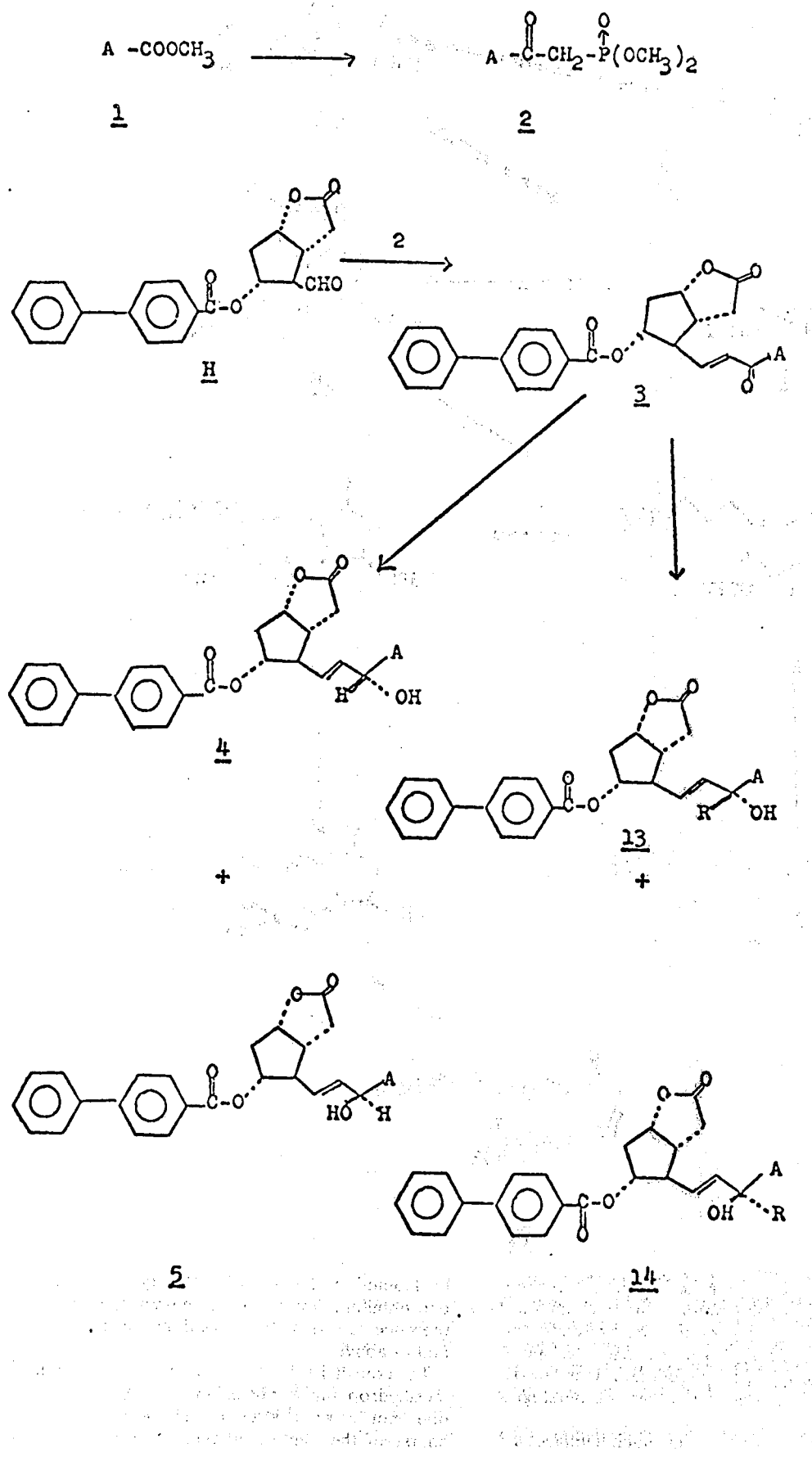

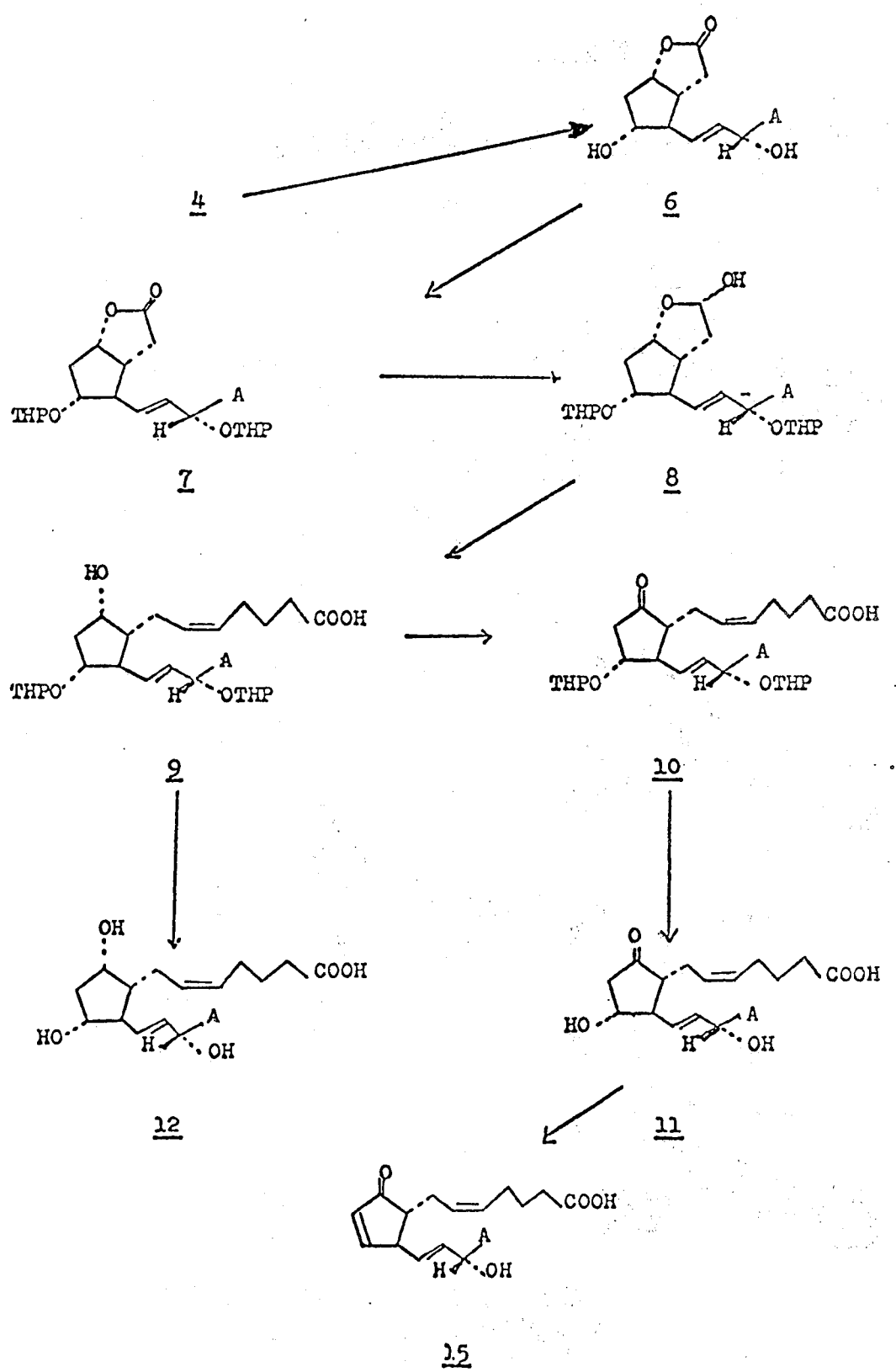

7 → 8 is a reduction of the lactone 7 to the hemiacetal 8 using diisobutyl aluminum hydride in an inert solvent. Low reaction temperatures are preferred and −60° to −70°C are usual. However, higher temperatures may be employed if over-reduction does not occur. 8 is purified, if desired, by column chromatography.

8 → 9 is a Wittig condensation in which hemiacetal 8 is reacted with (4-carbohydroxy-n-butyl)triphenylphosphonium bromide in dimethyl sulfoxide, in the presence of sodium methylsulfinyl methide. 9 is purified as above.

The conversion 9 → 12 is an acidic hydrolysis of the tetrahydropyranyl groups. Any acid may be used which does not cause destruction of the molecule in the course of the removal of the protecting group; however, this is accomplished most often by use of 65% aqueous acetic acid. The product is purified as above.

9 → 10 is an oxidation of the secondary alcohol 9 to the ketone 10. This may be accomplished using any oxidizing agent which does not attack double bonds; however, the Jones reagent is usually preferred. The product is purified as above.

10 → 11 is carried out in the same manner as 9 → 12. The product is purified as above. Reduction of the compound 11 with sodium borohydride will provide the 9β isomer of prostaglandin analogs of the F series, i.e. $PGF_{2\beta}$ Compounds. These may also be obtained via sodium borohydride reduction of 10 followed by hydrolysis as described above for 10 → 11.

11 → 15 is an acid-catalyzed dehydration. Any acid may be used for the process which does not cause extensive decomposition of the product, but the most usual procedure consists of dissolving 11 in an excess of 97% formic acid followed by dilution with ice water and extraction of the product after the starting material has been consumed. The product is purified as above.

Scheme C

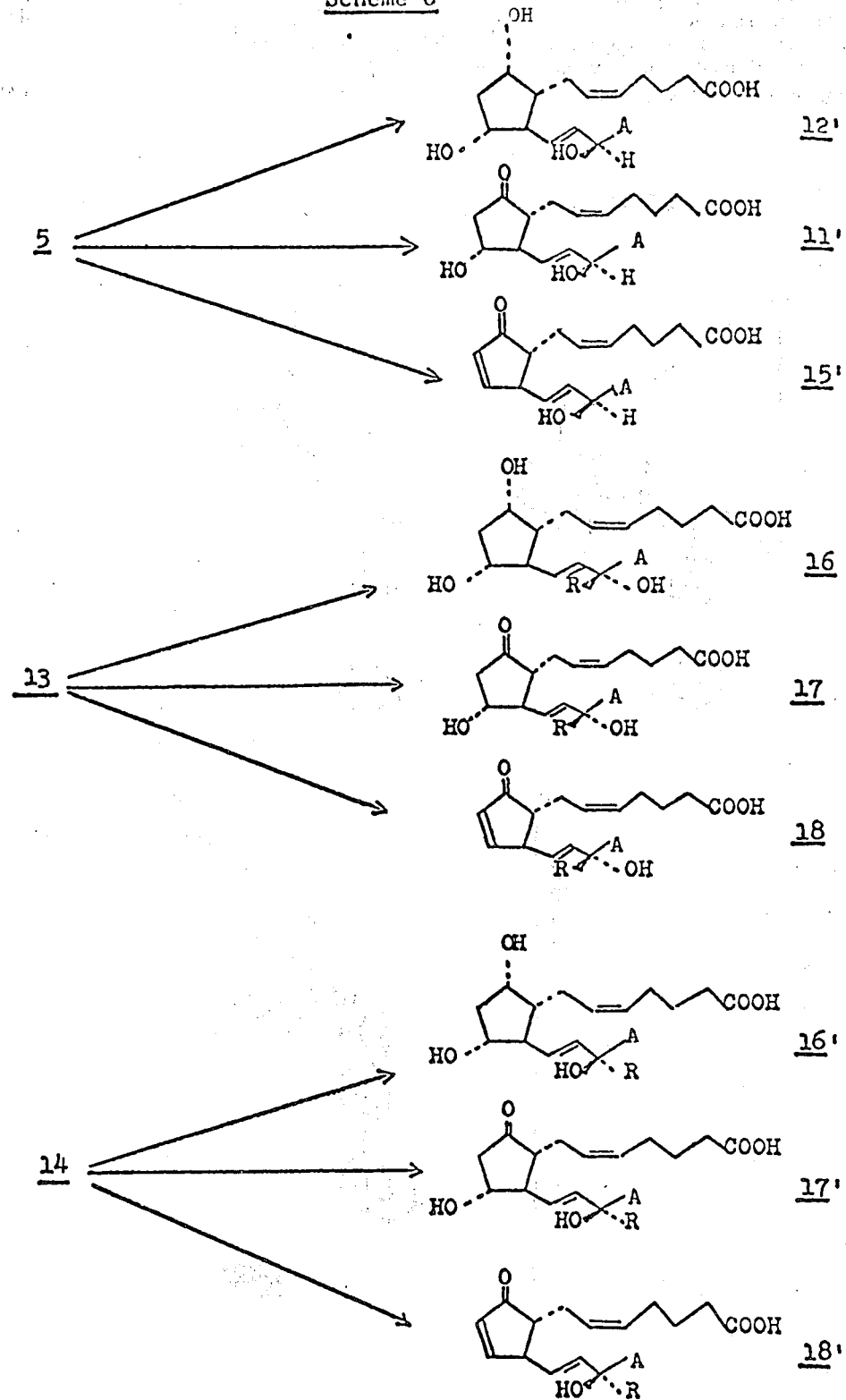

As is illustrated in scheme C, 5, 13 and 14 may be substituted for 4 in scheme B to provide prostaglandin derivatives 11'–12', 16'–18' and 16–18.

Scheme D illustrates the synthesis of precursors to the 13,14-dihydro-15-substituted-ω-pentanorprostaglandins.

In 3 → 19 ± 19' the enone 3 is reduced to the tetrahydro compound through the use of any of the complex metal hydride reducing agents, LiAlH$_4$, NaBH$_4$, KBH$_4$, LiBH$_4$ and Zn(BH$_4$)$_2$. Especially preferred is NaBH$_4$. The products, 19 and 19', are separated from each other by column chromatography.

Furthermore, the compounds 4 and 5 of Scheme A can be reduced catalytically with hydrogen to 19 and 19' respectively. The stage at which the double bond is reduced is not critical, and hydrogenation of 6 or 7 of scheme B will also afford useful intermediates for the 13,14-dihydroprostaglandin analogs of the present invention. This reduction may be achieved with either a homogenous catalyst such as tris-(triphenylphosphine)chlororodium I or with a heterogeneous catalyst such as platinum, palladium or rhodium. In a similar way the precursors to the 15-lower alkyl-15-substituted-ω-pentanorprostaglandins are synthesized by substituting compounds 13 and 14 for 4 and 5 respectively, in the synthesis just described. The conversion of 19, 19', 20' and 20 to their respective prostaglandins follows the route shown in scheme B when 4 is replaced by 19, 19', 20' and 20 to yield the 13,14-dihydro-PGE$_2$, -PGA$_2$ and -PGF$_2$ series of prostaglandin derivatives containing hydrogen or lower alkyl group at carbon 15.

Scheme D

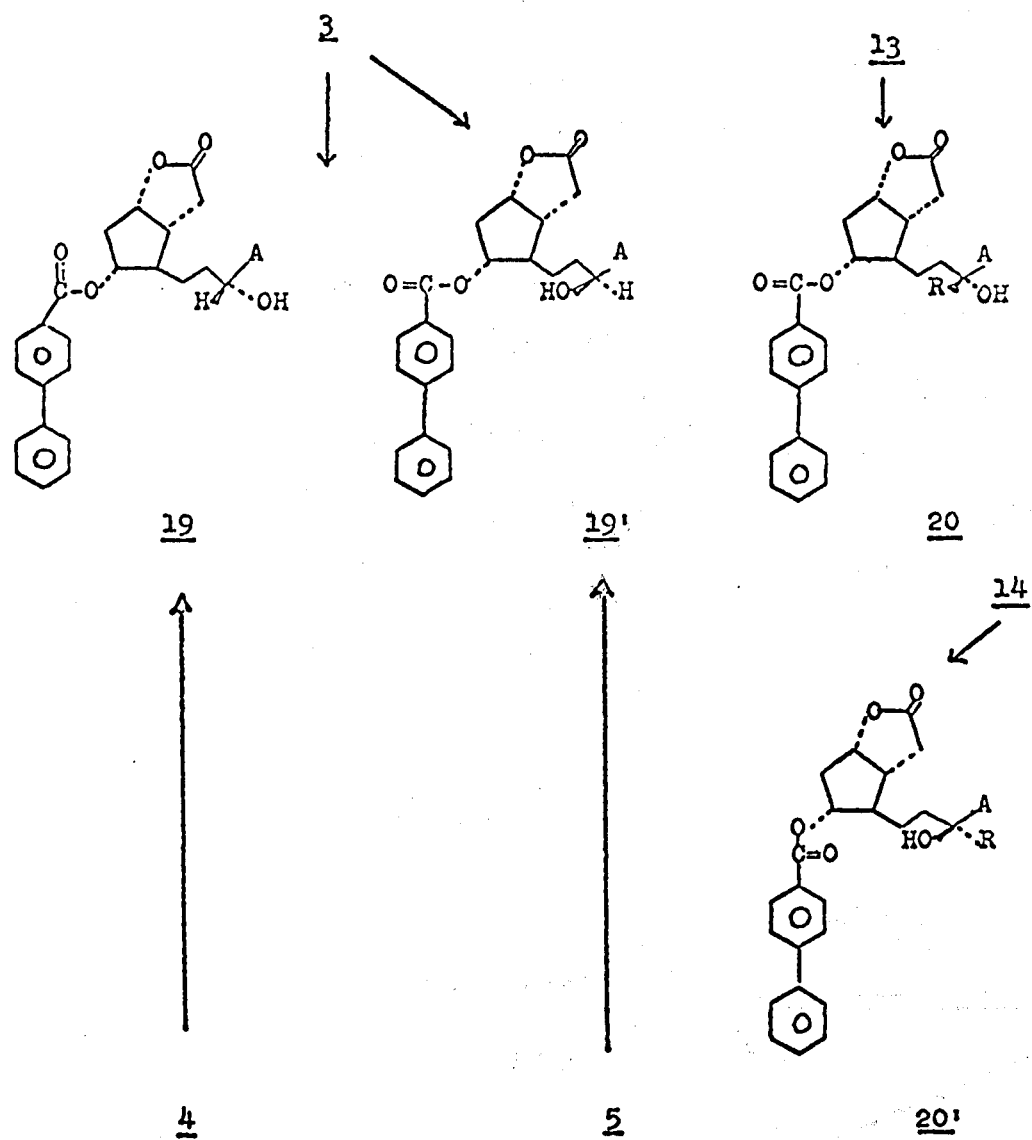

Scheme E illustrates the preparation of the various reduced 15-substituted-ω-pentanorprostaglandin precursors:

19 → 22 is carried out as illustrated on Scheme B for 4 → 9. 22 can be used as a precursor to a 13,14-dihydro-15-substituted-ω-pentanorprostaglandin of the "2-series" or as an intermediate to 23, a precursor to a 13,14-dihydro-15-substituted-ω-pentanorprostaglandin of the "1-series". 22 → 23 is carried out by catalytic hydrogenation using the catalyst described for the reduction of 4 → 19 of Scheme D. Intermediates of the type 21 are prepared by selective reduction of the 5,6 cis double bond at low temperature using catalysts such as those described for 4 → 19 and 17 → 23. Especially preferred for this reduction is the use of palladium on carbon as a catalyst and a reaction temperature of −20°. Intermediates of the type 21 are not only precursors to 15-substituted-ω-pentanorprostaglandins of the "1-series" through the route 9 → 15 of scheme B, but also as precursors to compounds of the type 23 through the route already discussed for 22 → 23. Furthermore, the 15-substituted-ω-pentanorprostaglandins of the $E_1$ and $F_{1\alpha}$ series may be obtained directly from the corresponding prostaglandin analogs of the "2-series" by first protecting the hydroxyl by introducing dimethyl isopropyl silyl groups, reducing selectively the cis double bond, and removing the protecting group.

Schema E

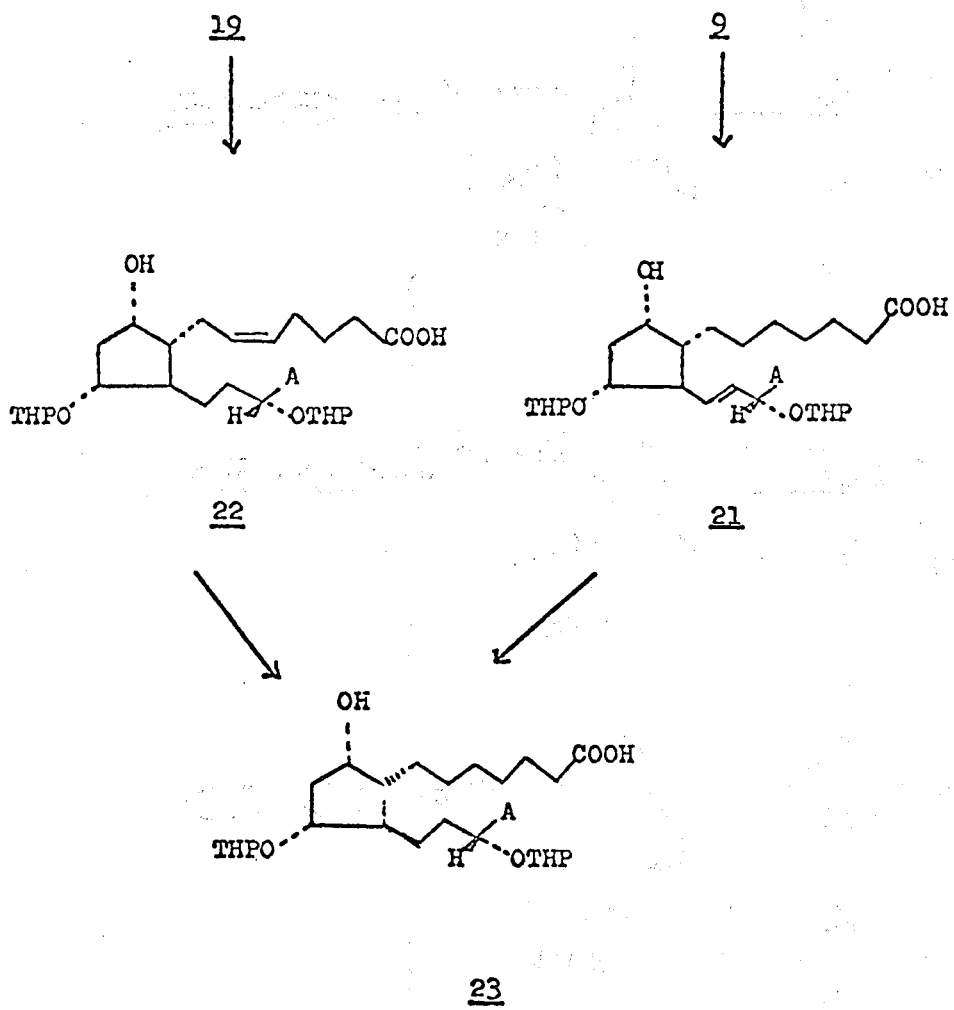

The introduction of the protecting group is usually accomplished by treatment of the prostaglandin analog with dimethyl isopropyl chlorosilane and triethylamine, the reduction is accomplished as discussed above for 9 → 21 and removal of the protecting group is accomplished by contacting the reduced protected compound with 3:1 acetic acid:water for 10 minutes or until reaction is substantially complete.

The $C_{15}$ epimers of 21, 22 and 23 can be used as precursors to the 15-epi series of prostaglandin derivatives described above, and 15-lower-alkyl-15-substituted-ω-pentanor-prostaglandins reduced at the 5,6 and-/or the 13,14 position and their $C_{15}$ epimers can be prepared from the appropriately substituted analogs of 9 and 19 whose syntheses follow those of Scheme A and B.

13,14-dihydro-15-lower alkyl-15-substituted-ω-pentanor-prostaglandins are available from the appropriately substituted precursors via Scheme E.

The synthesis of the natural prostaglandins has been performed by Prof. E. J. Corey and his co-workers (Corey, et al., *J. Amer. Chem. Soc.*, 92, 2586 (1970); and references cited therein), and prostaglandins made by this reaction sequence as well as those made by other schemes or isolated from natural material are suitable for use as precursors to the compounds of this invention.

The novel p-biphenyl esters of this invention can be prepared in several different ways. These differ from one another in that the p-biphenyl moiety is attached to the prostaglandin or its percurser at different stages of its synthesis.

For example scheme F shows three different routes to the p-biphenyl esters ("PBE").

In each case the p-biphenyl group is introduced by an esterification reaction which may be conducted most conveniently by contacting the appropriate prostaglandin or its precurser with about 1–10 moles of p-phenylphenol in the presence of 1–2 moles of dicyclohexylcarbodiimide in a reaction-inert solvent, typically methylene chloride. Any prostaglandin or prostaglandin analog may be used as a substrate for the above esterification reaction, and additionally precursors to such prostaglandins or prostaglandin analogs may also be used as illustrated in scheme F. For example, 9 may be converted to 9 PBE by the esterification reaction alluded to above and 9 PBE may then be converted to 10 PBE and 12 PBE by the same methods used to convert 9 to 10 and 12 as previously discussed. Compound 10 PBE may be converted to 11 PBE by reactions described for the conversion of 10 to 11.

SCHEME F

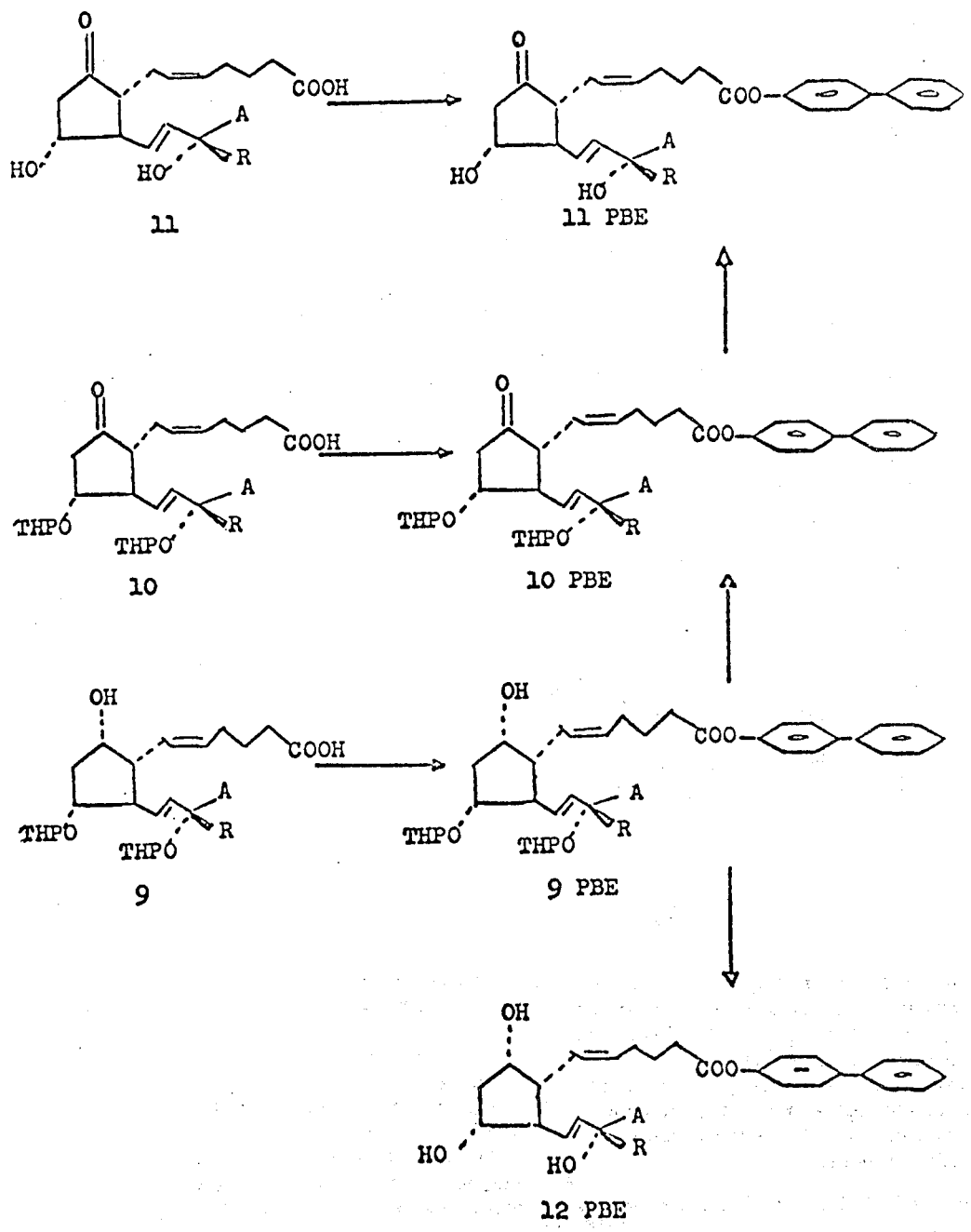

As is obvious from the above, the p-biphenyl esters such as 9 PBE, 10 PBE, 11 PBE and 12 PBE may be used as substrates for the various reductive schemes previously described for the production of the prostaglandin analogs of the "one" and "zero" series to produce the corresponding p-biphenyl ester of the "one" and "zero" series.

The p-biphenyl esters of prostaglandin analog acylated at $C_{11}$ and $C_{15}$ are readily prepared from the corresponding parent by acylation which is usually carried out using carboxylic acid anhydride as the acylation agents. To prepare formyloxy derivatives the mixed anhydrides (e.g., formic-acetic anhydride) is employed. The $C_9$, $C_{11}$ and $C_{15}$ acyloxy p-biphenyl esters of prostaglandin analogs are prepared in the same way from the desired PGF precurser.

In the foregoing procedures, where purification by chromatography is desired, appropriate chromatographic supports include neutral alumina and silica gel, and 60–200 mesh silica gel is generally preferred. The chromatography is suitably conducted in reaction-inert solvents such as ether, ethyl acetate, benzene, chloroform, methylene chloride, cyclohexane or n-hexane, as further illustrated in the appended examples.

In vivo and in vitro tests demonstrate that the new p-bi-phenyl esters of prostaglandins and their analogs possess physiological activities comparable to those exhibited by the natural prostaglandins (see above). These tests include, among others, a test for effect on isolated smooth muscle from guinea pig uterus, guinea pig ileum and rat uterus, inhibition of norepinephrine-induced lipolysis in isolated rat fat cells, inhibition of histamine-induced bronchospasm in the guinea pig, effect on dog blood pressure, inhibition of stress-induced ulceration in the rat, inhibition of gastric acid and pepsin secretion in rat and dog, inhibition of ADP- or collagen-induced aggregation of blood platelets, and effect on diarrhea in mice.

The physiological responses observed in these tests are useful in determining the utility of the test substance for the treatment of various natural and pathological conditions. Such determined utilities include: antihypertensive activity, bronchodilator activity, antithrombogenic activity, antiulcer activity, smooth muscle activity [useful as an anti-fertility agent, for the induction of labor, and as an abortifacient], and anti-fertility activity through a mechanism not affecting smooth muscle, for example, luteolytic mechanisms [useful as an agent for the regulation of the estrous cycle in livestock animals].

Further examples of the utility of the parent compounds whose p-biphenyl esters have similar activity and are likewise crystalline will be found in copending applications Ser. No. 259,215 of June 2, 1972 and Ser. No. 271,220 of July 13, 1972, and the disclosures thereof are incorporated herein by reference.

Another example of the high potency, specificity and crystallinity of the novel compounds of the present invention is 19-oxaprostaglandin $E_2$ p-biphenyl ester and the p-biphenyl esters of 17-aryl-$\omega$-trisnorprostaglandin $E_2$ or $F_{2\alpha}$ which have high smooth muscle activity useful for antifertility and abortifacient purposes. The novel 15-lower alkyl compounds of this invention have the same profile of activity as the prostaglandin analogs of this invention, where R is hydrogen, from which they are derived. The prostaglandin analogs which have a beta hydroxyl at C–15 and possess a C–15 lower alkyl group have action which is similar to their C–15 epimers. In some cases, however, the selectivity that these compounds display exceeds that of the epimeric compounds.

The prostaglandins having a $\beta$-hydroxyl at C–15 are in general less potent, although frequently more selective, than the corresponding $\alpha$-hydroxyl epimers. Additionally the prostaglandins having a $\beta$-hydroxyl at C–15 are valuable intermediates to prostaglandins having an $\alpha$-hydroxyl at C–15 through a recycling process involving an oxidation and reduction at C–15. A further example of the high selectivity, crystallinity and potency of the novel compounds of the present invention is 13,14-dihydro 16 phenyl-$\omega$-tetranor $PGF_{2\beta}$ which has highly selective hypotensive activity, a long duration of action, a potency of 3–4 times that of $PGE_2$ and a melting point of 129°–131°.

The p-biphenyl esters of natural prostaglandins are likewise easily crystallized and have the therapeutic properties of the prostaglandins from which they are derived. These properties are described in the "background of the invention."

The p-biphenyl esters of the prostaglandin analogs of the invention which are acylated at any or all available hydroxyl-bearing carbons have the same utilities as the unacylated species.

Although the prescribing physician will determine the optimum dosage for a given patient, the dosages will generally fall within the ranges stated below.

For induction of abortion an aqueous suspension of a 17-substituted-$\omega$-trisnorprostaglandin p-biphenyl ester of the E or F series or tablets of the same may appropriately be administered at oral doses of about 1–20 mg., with 1–7 doses per day being employed. For such treatment the oxaprostaglandin p-biphenyl esters may appropriately be administered at a level of from about 5 to 100 mg. with from 1 to 5 oral doses per day being employed. For intravaginal administration a suitable formulation would be lactose tablets or an impregnated tampon of the same agents. For such treatments suitable doses range from about 1–20 mg/dose for the p-biphenyl ester of the 17-phenyl $PGE_2$ derivative, from about 10–20 mg/dose for the p-biphenyl ester of the 17-phenyl $PGF_{2\alpha}$ derivative with 1 to 7 doses being employed, or from about 10–100 mg of an oxaprostaglandin p-biphenyl ester with 1–2 doses being employed.

Alternatively, for abortion, the 17-substituted-$\omega$-trisnor-prostaglandin p-biphenyl esters can be administered intraamniotically at doses of 5–40 mg, 1–5 times per day, or infused intravenously at doses of 5–500 $\mu$g/minute for a period of from about 1–24 hours.

Another suitable utility for the p-biphenyl esters of the 17-Ar-substituted prostaglandin analogs of this invention is to synchronize estrous in domestic animals. For this utility a suitable formulated 17-substituted-$\omega$-trisnor $PGF_{2\alpha}$ or $PGE_2$ p-biphenyl ester can be employed as an IM injection of about 0.25–50 mg per injection with from 1–3 injections.

Another suitable use for the p-biphenyl esters of the 17, 18, 19, and 20-Ar-substituted prostaglandin analogs and oxaprostaglandin of this invention is as inducers of labor. For this purpose an ethanol-saline solution of a 17-substituted-ω-trisnor-PGF$_{2\alpha}$ or PGE$_2$ p-biphenyl ester can be employed as an intravenous infusion in the amount of from about 0.05–50 μg/minute for from about 1–10 hours.

To produce bronchodilation or to increase nasal patency, an appropriate dosage form is an aqueous ethanolic solution of the p-biphenyl ester of 16-Ar-substituted-ω-tetranor PGE$_1$ or PGE$_2$ employed as an aerosol using fluorinated hydrocarbons as propellant in the amount of from about 3–500 μg/dose.

The p-biphenyl esters of the 15-substituted-ω-pentanor-prostaglandins of the A series as well as those of the 16-Ar-substituted-ω-tetranorprostaglandins of the Eo and 13,14-dihydro E$_2$, A$_2$ and F$_{2\beta}$ series, are useful hypotensive agents. Similarly the p-biphenyl esters of the 15-AR-substituted-ω-pentanorprostaglandins of the E series as useful as bronchodilators. For treatment of hypertension these drugs may appropriately be administered as an intravenous injection at doses of about 0.5–10 μg/kg or preferably in the form of capsules or tablets at doses of about 0.005 to 0.5 mg/kg/day.

The p-biphenyl esters of the 16-aryl-ω-tetranorprostaglandin of the E and A series are useful as antiulcer agents. For treatment of peptic ulcers these drugs may be administered in the form of capsules or tablets at doses of from 0.005 to 0.5 mg/kg/day.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohol, gums, polyalkylene glycols, petroleum jelly, cholesterol, and other known carriers for medicaments. If desired, these pharmaceutical compositions may contain auxiliary substances such as preserving agents, wetting agents, stabilizing agents, or other therapeutic agents such as antibiotics.

It will be seen that the formulae appearing in the foregoing depict optically active compounds. It will be clear, however, that the corresponding racemates will exhibit valuable biological activity by virtue of their content of the above-mentioned biologically active optical isomer, and it is intended that such racemates also be embraced by the foregoing formulae herein and in the appended claims. The racemic mixtures are readily prepared by the same methods employed herein to synthesize the optically active species, by mere substitution of corresponding racemic precursors in place of optically active starting materials.

The following examples are merely illustrative, and in no way limit the scope of the appended claims. In these examples it will be appreciated that all temperatures are expressed in Centigrade; all melting and boiling poiints are uncorrected. Further examples of the synthesis of the prostaglandin analogs from which the p-biphenyl esters of this invention are prepared can be found in copending application Ser. No. 259215 of June 2, 1972 and Ser. No. 271,220 of July 13, 1972, and the disclosures thereof are incorporated herein by reference.

EXAMPLE 1

Dimethyl 2-Oxo-3-phenylpropylphosphonate (2a)

A solution of 6.2 g (50 mmoles) dimethyl methylphosphonate (Aldrich) in 125 ml dry tetrahydrofuran was cooled to −78° in a dry nitrogen atmosphere. To the stirred phosphonate solution was added 21 ml of 2.37 M n-butyllithium in hexane solution (Alfa Inorganics, Inc.) dropwise over a period of 18 minutes at such a rate that the reaction temperature never rose above −65°. After an additional 5 minutes stirring at −78°, 7.5 g (50.0 mmole) methyl phenylacetate was added dropwise at a rate that kept the reaction temperature less than −70° (20 minutes). After 3.5 hours at −78°, the reaction mixture was allowed to warm to ambient temperature, neutralized with 6 ml acetic acid and rotary evaporated (water aspirator) to a white gel. The gelatinous material was taken up in 75 ml water, the aqueous phase extracted with 100 ml portions of chloroform (3×), the combined organic extracts were backwashed (50 cc H$_2$O), dried (MgSO$_4$), and concentrated (water aspirator) to a crude residue and distilled, b.p. 134°–5° (<0.1 mm) to give 3.5 g (29% dimethyl 2-oxo-3-phenylpropyl-phosphonate (2a).

The nmr spectrum (CDCl$_3$) showed a doublet centered at 3.7 δ(J = 11.5 cps, 6H) for

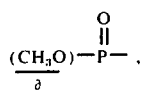

a doublet centered at 0.4 δ(J = 23 cps, 2H)

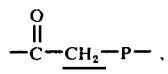

a singlet at 3.88 δ (2H) for

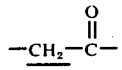

and a broad singlet at 7.22 δ(5H) for C$_6$H$_5$—.

In the manner described above dimethyl 2-oxo-3(p-chlorophenyl)propylphosphonate, dimethyl 2-oxo-3(p-phenylphenyl) propylphosphonate and dimethyl 2-oxo-3(m-methylphenyl) propylphosphonate may be prepared from the appropriately substituted methyl phenyl acetates. These products are suitable for conversion to the corresponding 16-substituted-ω-tetranor prostaglandin p-biphenyl esters by the sequence described below.

EXAMPLE 2

2-[3α-n-Phenylbenzoyloxy-5α-hydroxy-2β-(3-oxo-4-phenyl-trans-1-buten-1-yl) cyclopent-1α-yl]Acetic Acid, γ-lactone-(3a)

Method A

Dimethyl 2-oxo-3-phenylpropylphosphonate (2a) (3.4 g., 14.2 mmole) in 200 ml anhydrous ether was treated with 5.0 ml (12.5 mmole) 2.5 M n-butyllithium in n-hexane (Alfa Inorganics, Inc.) in a dry nitrogen atmosphere at room temperature. After 5 min. of stirring, an additional 400 ml. of anhydrous ether was added followed by 3.85 g (11 mmole) 2-[3α-p-phenyl-benzoyloxy-5α-hydroxy-2β-formylcyclopentan-1α-yl]acetic acid, γ-lactone in one portion and 50 ml anhydrous ether. After 35 minutes the reaction mixture was quenched with 5 ml glacial acetic acid, washed with 100 ml saturated sodium bicarbonate solution (4 ×), 100 ml water (2 ×), 100 ml saturated brine (1 ×), dried (MgSO₄) and evaporated to yield 2.908 g (57%) 2-[3α-p-phenylbenzoyloxy-5α-hydroxy-2β-(3-oxo-4-phenyl-trans-1-buten-1-yl)cyclopent-1α-yl]acetic acid, γ-lactone (3a) as a foam after column chromatography (silica gel, Baker, 60–200 mesh).

Method B

Dimethyl 2-oxo-3-phenylpropylphosphonate (2a) (2.9 g., 12 mmole) in 20 ml anhydrous dimethoxyethane was treated with 4.7 ml. (11 mmole) 2.34 M n-butyllithium in n-hexane (Alfa Inorganics, Inc.) in a dry nitrogen atmosphere at room temperature. After 40 min. of stirring, 3.5 g. (10 mmole) 2-[3α-p-phenylbenzoyloxy-5α-hydroxy-2β-formylcyclopentan-1α-yl]acetic acid, γ-lactone was added in one portion followed by 15 ml anhydrous 1,2-dimethoxyethane. After 30 minutes the reaction mixture was quenched with 1 ml glacial acetic acid, filtered, washed with 20 ml saturated sodium bicarbonate solution (2 ×), 20 ml saturated brine (1 ×), dried (Na₂SO₄) and evaporated to yield 2 g (43%) 2-[3α-p-phenylbenzoyloxy-5α-hydroxy-2β-(3-oxo-4-phenyl-trans-1-buten-1-yl)cyclopent-1α-yl]acetic acid, γ-lactone (3a) as a Foam after column chromatography (silica gel, Baker, 60–200 mesh).

The ir spectrum (CHCl₃) of the product (3a) exhibited adsorption bands at 1775 cm⁻¹ (strong), 1715 cm⁻¹ (strong), 1675 cm⁻¹ (medium) and 1630 cm⁻¹ (medium) attributable to the carbonyl groups and at 973 cm⁻¹ for the trans double bond. The nmr spectrum (CDCl₃) exhibited a multiplet at 7.23–8.18 δ (9H) for the p-biphenyl group, a doublet of doublets centered 6.27 δ(1H, J = 16 cps) and a doublet centered at 6.27 δ(1H, J = 1 cps) for the olefinic protons, a broad singlet at 7.20 (5H) for

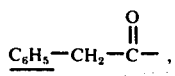

a singlet at 3.84 δ(2H) for

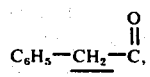

and multiplets at 4.90–5.50 δ(2H) and 2.21–3.07 δ(6H) for the remainder of the protons.

EXAMPLE 3

2-[3α-p-Phenylbenzoyloxy-5α-hydroxy-2β-(3α-hydroxy-4-phenyl-trans-1-buten-1-yl)cyclopent-1α-yl]acetic acid, γ-lactone (4a) and
2-[3α-n-Phenylbenzoyloxy-5α-hydroxy-2β-(3β-hydroxy-4-phenyl-trans-1buten-1-yl)cyclopent-1α-yl]acetic acid γ-lactone (5a)

To a solution of 2908 mg (6.2 mmole) 2-[3α-p-phenylbenzoyl-oxy-5α-hydroxy-2β-(3-oxo-4-phenyl-trans-1-buten-1-yl)cyclopent-1a-yl]acetic acid, γ-lactone (3a) in 30 ml dry 1,2-dimethoxyethane in a dry nitrogen atmosphere at ambient temperature was added dropwise 2.0 ml. of a 1.0 M zinc borohydride solution in 1,2-dimethoxyethane. After stirring at 0° for 2 hours, a saturated sodium bitartrate solution was added dropwise until hydrogen evolution ceased. The reaction mixture was allowed to stir for 5 minutes at which time 250 ml dry methylene chloride was added. After drying (MgSO₄) and concentrating (water aspirator) the resultant semisolid was purified by column chromatography on silica gel (Baker "Analyzed" Reagent 60–200 mesh) using ether as eluent. After elution of less polar impurities a fraction containing 658 mg 2-[3α-p-phenylbenzoyloxy-5α-hydroxy-2β-(3α-hydroxy-4-phenyl-trans-1-buten-1-yl)cyclopent-1α-yl]acetic acid, γ-lactone (4a), a 480 mg fraction of mixed 4a and 5a and finally a fraction (671 mg) of 2-[3α-p-phenylbenzoyloxy-5α-hydroxy-2β-(3β-hydroxy-4-phenyl-trans-1-buten-yl)cyclopent-1α-yl]acetic acid, γ-lactone (5a).

The ir spectrum (CHCl₃) of 4a and 5a had strong carbonyl absorptions at 1770 and 1715 cm⁻¹ and an absorption at 970 cm⁻¹ for the trans double bond. The NMR spectrum (CDCl₃) of 4a and 5a was consistent with the assigned structure.

EXAMPLE 4

2[3α,5α-Dihydroxy-2β-(3α-hydroxy-4-phenyl-trans-1-buten-1-yl) cyclopent-1α-yl]acetic acid, γ-lactone (6a)

A heterogeneous mixture of 658 mg (1.35 mmole) of 2-[3α-p-phenylbenzoyloxy-5α-hydroxy-2β-(3α-hydroxy-4-phenyl-trans-1-buten-1-yl)cyclopent-1α-yl]acetic acid, γ-lactone (4a), 7.1 ml. of absolute methanol and 188 mg. of finely powdered, anhydrous potassium carbonate was stirred at room temperature for 1 hour then cooled to 0°. To the cooled solution was added 2.8 ml (2.8 mmole of 1.0N aqueous hydrochloric acid. After stirring at 0° for an additional 10 minutes, 5 ml. of water was added with concomitant formation of methyl p-phenylbenzoate which was collected by filtration. The filtrate was saturated with solid sodium chloride, extracted with ethyl acetate (4 × 10 ml.), the combined organic extracts were washed with saturated sodium bicarbonate (10 ml.), dried (MgSO₄) and concentrated to give 381 mg of viscous, oily 2-[3α,5α-dihydroxy-2β-(3α-hydroxy-4-phenyl-trans-1-buten-1-yl)cyclopent-1α-yl]acetic acid, γ-lactone (6a).

The ir spectrum (CHCl₃) exhibited a strong absorption at 1770 cm⁻¹ for the lactone carbonyl and medium absorption at 965 cm⁻¹ for the trans-double bond.

EXAMPLE 5

2-[3α,5α-Dihydroxy-2β-(3β-hydroxy-4-phenyl-trans-1-buten-1-yl) cyclopent-1α-yl]acetic acid, γ-lactone (6'a)

A heterogeneous mixture of 761 mg (1.57 mmole) of 2-[3α-p-phenylbenzoyloxy-5α-hydroxy-2β-(3β-hydroxy-4-phenyl-trans-1-buten-1-yl)cyclopent-1α-yl]acetic acid, γ-lactone (5a), 7.1 ml. of absolute methanol and 216 mg of finely powdered, anhydrous potassium carbonate was stirred at room temperature for 1 hour, then cooled to 0°. To the cooled solution was added 3.2 ml (3.2 mmole) of 1.0N aqueous hydrochloric acid. After stirring at 0° for an additional 10 minutes, 5 ml. of water was added with concomitant formation of methyl p-phenylbenzoate which was collected by filtration. The filtrate was saturated with solid sodium chloride, extracted with ethyl acetate (4 × 10 ml.), the combined organic extracts were washed with saturated sodium bicarbonate (10 ml) dried (MgSO₄) and concentrated to give 382 mg (85%) of viscous oily 2-[3α,5α-dihydroxy- 2β-(3β-hydroxy-4-phenyl-trans-1-buten-1-yl)cyclopent-1α-yl]acetic acid, γ-lactone (6'a).

The ir spectrum (CHCl₃) exhibited a strong absorption at 1770 cm⁻¹ for the lactone carbonyl and medium absorption at 1965 cm⁻¹ for the trans-double bond.

EXAMPLE 6

2-[5α-Hydroxy-3α-(tetrahydropyran-2-yloxy)-2β-(3α-[tetrahydropyran-2-yloxy]-4-phenyl-trans-1-buten-1-yl)cyclopent-1α-yl]acetic acid, γ-lactone (7a)

To a solution of 38 mg (1.33 mmole) 2-[3α,5α-dihydroxy-2β-(3α-hydroxy-4-phenyl-trans-1-buten-yl)cyclopent-1α-yl]acetic acid, γ-lactone (6a) in 5 ml anhydrous methylene chloride and 0.4 ml of 2,3-dihydropyran at 0° in a dry nitrogen atmosphere was added 5 ml p-toluenesulfonic acid monohydrate. After stirring for 15 minutes, the reaction mixture was combined with 100 ml ether, the ether solution washed with saturated sodium bicarbonate (1 × 15 ml) then saturated brine (1 × 15 ml), dried (MgSO₄) and concentrated to yield 615 mg (>100%) crude 2-[5α-hydroxy-3α-(tetrahydropyran-2-yloxy)-2β-(3α-[tetrahydropyran-2-yloxy]-4-phenyl-trans-1-buten-1-yl)cyclopent-1α-yl]acetic acid, γ-lactone (7a).

The product of this example (7a) may be converted to 13,14-dihydro-16-phenyl-ω-tetranorprostaglandins of the A, E or F series through the procedures of examples 16, 18, 20–24.

EXAMPLE 7

2-[5α-Hydroxy-3α-(tetrahydropyran-2-yloxy)-2β-(3β-[tetrahydropyran-2-yloxy]-4-phenyl-trans-1-buten-1-yl)cyclopent-1α-yl]acetic acid, γ-lactone (7'a)

To a solution of 382 mg (0.71 mmole) 2-[3α,5α-dihydroxy-2β-(3β-hydroxy-4-phenyl-trans-1-butenyl)cyclopent-1α-yl]acetic acid, γ-lactone (6'a) in 5 ml anhydrous methylene chloride and 0.4 ml of 2,3-dihydropyran at 0° in a dry nitrogen atmosphere was added 5 mg p-toluenesulfonic acid monohydrate. After stirring for 15 minutes, the reaction mixture was combined with 100 ml ether, the ether solution washed with saturated sodium bicarbonate (1 × 15 ml) then saturated brine (1 × 15 ml), dried (MgSO₄) and concentrated to yield 621 mg (>100%) crude 2-[5α-hydroxy-3α-(tetrahydropyran-2-yloxy)-2β-(3β-[tetrahydropyran-2-yloxy]-4-phenyl-trans-1-buten-1-yl)cyclopent-1α-yl]acetic acid, γ-lactone (7'a).

The nmr spectrum (CDCl₃) of 7a and 7'a exhibited a multiplet at 5.30–5.62 δ (2H) for the olefinic protons, a singlet at 7.2 δ (5H) for the phenyl protons, and multiplets at 4.36–5.18 δ (4H), 3.22–4.24 δ (9H), and 1.18–2.92 δ (16H) for the remaining protons. The ir (CHCl₃) spectrum had a medium absorption at 970 cm⁻¹ for the trans-double bond.

EXAMPLE 8

2-[5α-Hydroxy-3α-(tetrahydropyran-2-yloxy)-2β-(3β-[tetrahydropyran-2-yloxy]-4-phenyl-trans-1-buten-1-yl) cyclopent-1α-yl] acetaldehyde, γ-hemiacetal (8a)

A solution of 605 mg (1.33 mmole) 2-[5α-hydroxy-3α-(tetrahydropyran-2-yloxy)-2β-3β-[tetrahydropyran-2-yloxy]-4-phenyl-trans-1-buten-1-yl)cyclopent-1α-yl]acetic acid, γ-lactone (7a) in 8 ml dry toluene was cooled to −78° in a dry nitrogen atmosphere. To this cooled solution was added 3.0 ml of 20% diisobutylaluminum hydride in n-hexane (Alfa Inorganics) dropwise at such a rate so that the internal temperature never rose above −65° (15 minutes). After an additional 45 minutes of stirring at −78°, anhydrous methanol was added until gas evolution ceased and the reaction mixture was combined with 100 ml ether, washed with 50% sodium potassium tartrate solution (4 × 20 ml), dried (Na₂SO₄) and concentrated to yield 615 mg (100%) 2-[5α-hydroxy-3α-(tetrahydropyran-2-yloxy)-2β-(3α-[tetrahydropyran-2-yloxy]-4-phenyl-trans-1-buten-1-yl)cyclopent-1-yl]acetaldehyde, γ-hemiacetal (8a).

EXAMPLE 9

2-[5α-Hydroxy-3α-(tetrahydropyran-2-yloxy)-2β-(3β-[tetrahydropyran-2-yloxy]-4-phenyl-trans-1-buten-1-)ylcyclopent-1α-yl]acetaldehyde, γ-hemiacetal (8'a)

A solution of 621 mg (1.34 mmole) 2-[5α-hydroxy-3α-(tetrahydropyran-2-yloxy)-2β-(3β-[tetrahydropyran-2-yloxy]-4-phenyl-trans-1-buten-1-yl)cyclopent-1α-yl]acetic acid, γ-lactone (7'a) in 8 ml dry toluene was cooled to −78° in a dry nitrogen atmosphere. To this cooled solution was added 3.0 ml of 20% diisobutylaluminum hydride in n-hexane (Alfa Inorganics) dropwise at such a rate so that the internal temperature never rose above −60° (15 minutes). After an additional 45 minutes of stirring at −78° anhydrous methanol was added until gas evolution ceased and the reaction mixture was allowed to warm to room temperature. The reaction mixture was combined with 100 ml ether, washed with 50% sodium potassium tartrate solution (4 × 20 ml), dried (Na₂SO₄) and concentrated to yield 621 mg (100%) 2-[5α-hydroxy-3α-(tetrahydropyran-2-yloxy)-2β-(3β-[tetrahydropyran-2-yloxy]-4-phenyl-trans-1-buten-1-yl)cyclopent-1-yl]acetaldehyde, γ-hemiacetal (8'a).

EXAMPLE 10

9α-Hydroxy-11α,15α-bis-(tetrahydropuran-2-yloxy)-16-phenyl-cis-5-trans-13-ω-tetranor prostadienoic acid (9a)

To a solution of 1760 mg (4.0 mmole) (4-carbohydroxy-n-butyl) triphenylphosphonium bromide in a dry nitrogen atmosphere in 5.0 ml dry dimethyl sulfoxide was added 3.2 ml (7.0 mmole) of a 2.2M solution of sodium methylsufinylmethide in dimethyl sulfoxide. To this red ylide solution was added dropwise a solution of 615 mg (1.34 mmole) 2-[5α-hydroxy-3α-(tetrahydropyran-2-yloxy)-2β-(3α-[tetrahydropyran-2-yloxy]-4-phenyl-trans-1-buten-1-yl)cyclopent-1α-yl]acetaldehyde, γ-hemiacetal (8a) in 5.0 ml dry dimethyl sulfoxide over a period of 20 minutes. After an additional 2 hours stirring at room temperature, the reaction mixture was poured in ice water. The basic aqueous solution was washed twice with ethyl acetate (20 ml.) and acidified to pH ~3 with 10% aqueous hydrochloric acid. The acidic solution was extracted with ethyl acetate (3 × 20 ml) and the combined organic extracts washed once with water (10 ml.), dried (MgSO₄) and evaporated to a solid residue. This solid residue was triturated with ethyl acetate and filtered. The filtrate was purified by column chromatography on silica gel (Baker "Analyzed" Reagent 60–200 mesh) using ethyl acetate as eluent. After removal of high R_f impurities, 150 mg of 9α-hydroxy-11α,15α-bis-(tetrahydropyran-2-yloxy)-16-phenyl-cis-5-trans-13-ω-tetranor prostadienoic acid (9a) was collected.

This product (9a) is converted to its p-biphenyl ester by the procedure of example 28.

EXAMPLE 11

9α-Hydroxy-11α,15β-bis-(tetrahydropuran-2-yloxy)-16-phenyl-cis-5-trans-13-ω-tetranor prostadienoic acid (9'a)

To a solution of 1760 mg (4.0 mmole) (4-carbohydroxy-n-butyl) triphenylphosphonium bromide in a dry nitrogen atmosphere in 5.0 ml dry dimethyl sulfoxide was added 3.2 ml (7.0 mmole) of a 2.2M solution of sodium methylsulfinylmethide in dimethyl sulfoxide. To this red ylide solution was added dropwise a solution of 621 mg (1.34 mmole) 2-[5α-hydroxy-3α-(tetrahydropyran-2-yloxy)-2β-(3β-[tetrahydropyran-2-yloxy]-4-phenyl-trans-1-buten-1-yl)cyclopent-1α-yl]acetaldehyde, γ-hemiacetal (8'a) in 5.0 ml. dry dimethyl sulfoxide over a period of 20 minutes. After an additional 2 hours stirring at room temperature, the reaction mixture was poured into ice water. The basic aqueous solution was washed twice with ethyl acetate (20 ml.) and acidified to pH ~3 with 10% aqueous hydrochloric acid. The acidic solution was extracted with ethyl acetate (3 × 20 ml) and the combined organic extracts washed once with water (10 ml.), dried (MgSO$_4$) and evaporated to a solid residue. The solid residue was triturated with ethyl acetate and filtered. The filtrate was purified by column chromatography on silica gel (Baker "Analyzed" Reagent 60–200 mesh) using ethyl acetate as eluent. After removal of high R$_f$ impurities, 300 mg of 9α-hydroxy-11α,15β-bis-(tetra-hydropyran-2-yloxy)-16-phenyl-cis-5-trans-13-ω-tetranor prostadienoic acid (9'a) was collected.

EXAMPLE 12

9-Oxo-11α,15α,-bis-(tetrahydropyran-2-yloxy)-16-phenyl-cis-5-trans-13-ω-tetranor prostadienoic acid (10a)

To a solution cooled to −10° under nitrogen of 2300 mg (4.24 mmole) 9α-hydroxy-11α,15α-bis-(tetrahydropyran-2-yloxy)-16-phenyl-cis-5-trans-13-ω-tetranor prostadienoic acid (9a) in 50 ml. reagent grade acetone was added dropwise to 11.3 ml. (29.6 mmole) of Jones' reagent. After 20 minutes at −10°, 10 ml. 2-propanol was added and the reaction mixture was allowed to stir an additional 5 minutes at which time it was combined with 300 ml. ethyl acetate, washed with water (3 × 50 ml.), dried (MgSO$_4$) and concentrated to give 1983 mg. of 9-oxo-11α,15α-bis-(tetrahydropyran-2-yloxy)-16-phenyl-cis-5-trans-13-ω-tetranor prostadienoic acid (10a).

EXAMPLE 13

9-Oxo-11α,15β-bis-(tetrahydropyran-2-yloxy)-16-phenyl-cis-5-trans-13-ω-tetranor prostadienoic acid (10'a)

To a solution cooled to −10° under nitrogen of 300 mg (0.551 mmole) 9α-hydroxy-11α,15β-bis-(tetrahydropyran-2-yloxy)-16-phenyl-cis-5-trans-13-ω-tetranor prostadienoic acid (9'a) in 9.2 ml. reagent grade acetone was added dropwise to 0.262 ml. (0.655 mmole) of Jones' reagent. After 20 minutes at −10°, 0.260 ml. 2-propanol was added and the reaction mixture was allowed to stir an additional 5 minutes at which time it was combined with 75 ml. ethyl acetate, washed with water (3 × 10 ml.), dried (MgSO$_4$) and concentrated to give 220 mg. of 9-oxo-11α,15β-bis-(tetrahydropyran-2-yloxy)-16-phenyl-cis-5-trans-13-ω-tetranor-prostadienoic acid (10'a).

EXAMPLE 14

9-Oxo-11α,15α-dihydroxy-16-phenyl-cis-5-trans-13-ω-tetranor-prostadienoic acid (11a)

A solution of 1637 mg. (3.02 mmole) 9-oxo-11α,15α-bis-tetrahydropyran-2-yloxy)-16-phenyl-cis-5-trans-13-ω-tetranor-prostadienoic acid (10a) in 20 ml. of a 65:35 mixture of glacial acetic acid:water was stirred under nitrogen at room temperature for 24 hours and then was concentrated by rotary evaporation. The resultant crude oil was purified by column chromatography on silica gel (Mallinckrodt CC-4 100–200 mesh) using ethyl acetate-cyclohexane as eluent. After elution of less polar impurities, the oily 9-oxo-11α,15α-dihydroxy-16-phenyl-cis-5-trans-13-ω-tetranor-prostadienoic acid (11a) weighing 365 mg. was collected.

EXAMPLE 15

9-Oxo-11α,15β-dihydroxy-16-phenyl-cis-5-trans-13-ω-tetranor-prostadienoic acid (11'a)

A solution of 220 mg. (0.334 mmole) 9-oxo-11α,15α-bis-(tetrahydropyran-2-yloxy)-16-phenyl-cis-5-trans-13-ω-tetranor-prostadienoic acid (10'a) in 3.0 ml. of a 65:35 mixture of glacial acetic acid:water was stirred under nitrogen at 38° for 5 hours and then was concentrated by rotary evaporation. The resultant crude oil was purified by column chromatography on silica gel (Mallinckrodt CC-4 100–200 mesh) using ethyl acetate as eluent. After elution of less polar impurities the semisolid 9-oxo-11α,15β-dihydroxy-16-phenyl-cis-5-trans-13-ω-tetranor prostadienoic acid (11'a) weighing 8 mg. was collected. This product may be converted to its p-biphenyl ester by the procedure of example 27.

EXAMPLE 16

9α,11α,15α-Trihydroxy-16-phenyl-cis-5-trans-13-ω-tetranor-prostadienoic acid (12a)

A mixture of 0.7 g of 9α-hydroxy-11α,15α-bis-(tetrahydro-pyran-2-yloxy)-16-phenyl-cis-5-trans-13-ω-tetranorprostadienoic acid (9a) in 5 ml. of a 65:35 mixture of acetic acid:water was stirred under nitrogen at room temperature overnight, then was concentrated under reduced pressure to a viscous oil. The crude product was purified by column chromatography on Mallinckrodt CC-4 silica gel using ethyl acetate as eluent. After elution of less polar impurities, the desired 9α,11α,15α-trihydroxy-16-phenyl-cis-5-trans-13-ω-tetranor-prostadienoic acid (12a) was obtained as a viscous, colorless oil weighing 51 mg.

The ir spectrum (CHCl$_3$) of 12 showed a strong absorption at 1710 cm$^{-1}$ for the carbonyl group and a medium absorption at 970 cm$^{-1}$ for the trans double bond.

The product obtained above (12a) may be converted to 16-phenyl-ω-tetranor prostaglandin F$_{1α}$ via the process of Example 26. 12a may also be converted to 16-phenyl-ω-tetranor prostaglandin F$_{0\,α}$, via the process of Example 25. The above products may be converted to their p-biphenyl esters by the procedure of example 27.

EXAMPLE 17

2-[3α-p-Phenylbenzoyloxy-5α-hydroxy-2β-(3α-hydroxy-3β-methyl-4-phenyl-trans-1-buten-1-yl)cyclopent-1α-yl]acetic acid, γ-lactone (13α) and 2 [3α-p-Phenylbenzoyloxy-5α-hydroxy-2β(3β-hydroxy-3α-methyl-4-phenyl-trans-1-buten-1-yl)cyclopent-1α-yl]acetic acid γ-lactone (14a)

To a solution of 2908 mg (6.2 mmole) 2-[3α-p-phenyl-benzoyl oxy-5α-hydroxy-2β-(3-oxo-4-phenyl-trans-1-buten-1-yl) cyclopent-1α-yl]acetic acid, γ-lactone (3a) in 26 ml anhydrous ether and 20 ml of tetrahydrofuran (distilled from LAH) in a dry nitrogen atmosphere at −78° is added dropwise 6.8 ml of (0.92M) methyllithium in ether (Alfa). After stirring at −78° for 15 minutes the reaction is quenched by the dropwise addition of glacial acetic acid until the pH of the reaction is approximately 7. The mixture is then diluted with methylene chloride and the diluted organic solution is washed with water (1×) and with saturated brine (1×), is dried (anhydrous magnesium sulfate), and is concentrated to afford the epimeric alcohols.

The crude product is purified by column chromatography on 108 g. of silica gel (Baker "Analyzed" Reagent 60–200 mesh) using a mixture of benzene:ethyl acetate as eluent to provide the 2-[3α-p-phenylbenzoyloxy-5α-hydroxy-2β-(3α-hydroxy-3β-methyl-4-phenyl-trans-1-buten-1-yl)cyclopent-1α-yl]acetic acid, γ-lactone (13a), and 2-[3α-p-phenylbenzoyloxy-5α-hydroxy-2β-(3β-hydroxy-3α-methyl-4-phenyl-trans-1-buten-yl)cyclopent-1α-yl]acetic acid, γ-lactone (14a).

This material (14a) may be converted to the 15β-methyl-16-phenyl-ω-tetranorprostaglandins of the A, E, and F series by the procedures outlined in Examples 4–16 and 18–26. These may in turn be converted to their p-biphenyl esters by the procedure of example 27.

Other lower alkyl derivatives of the type (14a) may be prepared by substituting the appropriate alkyl lithium derivative for methyl lithium in the above procedure. These derivatives are suitable for conversion to 15-lower alkyl-16-phenyl-ω-tetranorprostaglandins of the A, E, and F series through the sequences of Examples 3–16 and 18–26.

EXAMPLE 18

9-oxo-15α-hydroxy-16-phenyl-cis-5-Δ$^{10,11}$-trans-13-ω-tetranor-prostatrienoic acid (15a)

A solution of 50 mg of 9-oxo-11α,15α-dihydroxy-16-phenyl-cis-5-trans-13-ω-tetranor-prostadienoic acid (11a) in 10 ml dry methylene chloride and 10 ml formic acid is stirred at room temperature for 5 hours. The reaction mixture is diluted with 50 ml toluene and evaporated to yield (after chromatography) 9-oxo-11α-hydroxy-16-phenyl-cis-5-Δ$^{10,11}$-trans-13-ω-tetranor prostadienoic acid (15a).

In the same way 15-substituted-ω-pentanor prostaglandins of the $A_1, A_0$ and 13,14 dihydro $A_2$ series may be prepared from 15-substituted-ω-pentanorprostaglandins of the $E_1, E_0$ and 13, 14-dihydro series respectively. This product may be converted to its p-biphenyl ester by the procedure of example 27.

EXAMPLE 19

The procedure of example 3 in which sodium borohydride is substituted for zinc borohydride may be used to produce 19a, 19a may then be converted to 24a via the procedure of example 4, which is further converted to 13,14 dihydro-16-phenyl-ω-tetranor prostaglandins of the A, E or F series by the procedures of examples 21–24, 16, and 18.

EXAMPLE 20

2-[5α-Hydroxy-3α(tetrahydropyran-2-yloxy)-2β-(3α-{tetrahydropyran-2-yloxy}-4-phenylbut-1-yl)cyclopent-1α-yl]acetic acid, γ-lactone (24a)

A stirred heterogeneous solution of 1.555 g (3.4 mmole) 2-[5α-hydroxy-3α(tetrahydropyran-2-yloxy)-2β-(3α{tetrahydropyran-2-yloxy}-4-phenyl-trans-1-buten-1-yl)cyclopent-1α-yl]acetic acid, γ-lactone (7a) and 300 mg 5% palladium on carbon in 35 ml. at absolute methanol was hydrogenated for 90 minutes. The reaction mixture was filtered through filter aid and concentrated (in vacuo) to yield 1.457 g of 2-[5α-hydroxy-3α(tetrahydropyran-2-yloxy)-2β-(3α-{tetrahydropyran-2-yloxy}-4-phenylbut-1-yl)cyclopentan-1α-yl]acetic acid, γ-lactone (24a). The ir spectrum ($CHCl_3$) of 24a exhibited a lactone carbonyl adsorbtion at 1770 $cm^{-1}$.

EXAMPLE 21

2-[5α-Hydroxy-3α-(tetrahydropyran-2-yloxy)-2β-(3α-{tetrahydropyran-2-yloxy}-4-phenylbut-1-yl)cyclopent-1α-yl]acetaldehyde, γ-hemiacetal (25a)

A solution of 1457 mg (3.2 mmole) 2-[5α-hydroxy-3α-(tetra-hydropyran-2-yloxy)-2β-(3α-{tetrahydropyran-2-yloxy}-4-phenylbut-1-yl)cyclopent-1α-yl] acetic acid, γ-lactone (24α) in 15 ml dry toluene was cooled to −78° in a dry nitrogen atmosphere. To this cooled solution was added 5.0 ml of 20% diisobutylaluminum hydride in n-hexane (Alfa Inorganics) dropwise at such a rate so that the internal temperature never rose above −65° (3 minutes). After an additional 30 minutes of stirring at −78°, anhydrous methanol was added until gas evolution ceased and the reaction mixture was allowed to warm to room temperature. The reaction mixture was combined with 150 ml ether, washed with 50% sodium potassium tartrate solution (1 × 50 ml), dried ($Na_2SO_4$) concentrated, and chromatagraphed to yield 1200 mg (81.5%) 2-[5α-hydroxy-3α-(tetrahydropyran-2-yloxy)-2β-(3α-{tetrahydropyran-2-yloxy}-4-phenylbut-1-yl)cyclopent-1-yl]acetaldehyde, γ-hemiacetal (25a).

EXAMPLE 22

9α-Hydroxy-11α,15α-bis-(tetrahydropyran-2-yloxy)-16-phenyl-cis-5-ω-tetranor prostenoic acid (22a)

To a solution of 5150 mg (11.6 mmole) (4-carbohydroxy-n-butyl) triphenylphosphonium bromide in a dry nitrogen atmosphere in 10.1 ml dry dimethyl sulfoxide was added 10.8 ml (21.1 mmole) of a 1.96M solution of sodium methylsufinylmethide in dimethyl sulfoxide. To this red ylide solution was added dropwise a solution of 1200 mg (2.6 mmole) 2-[5α-hydroxy-3α-(tetrahydropyran-2-yloxy)-2β-(3α-{tetrahydropyran-2-yloxy}-4-phenyl-but-1-yl)cyclopent-1α-yl]acetaldehyde, γ-hemiacetal (25a) in 7.0 ml dry dimethyl sulfoxide over a period of 20 minutes. After an additional 2 hours stirring at room temperature, the reaction mixture was poured into ice water. The basic aqueous solution was acidified to pH 3 with 10% aqueous hydrochloric acid. The acidic solution was extracted with ethyl acetate (3 × 100 ml) and the combined organic extracts washed once with water (50 ml.) dried (MgSo₄) and evaporated to a solid residue. This solid residue was triturated with ethyl acetate and filtered. The filtrate was purified by column chromatography on silica gel (Baker "Analyzed" Reagent 60–200 mesh) using ethyl acetate as eluent. After removal of high $R_f$ impurities, 880 mg of 9α-hydroxy-11α,15α-bis-(tetrahydropyran-2-yloxy)-16-phenyl-cis-5-ω-tetranor prostenoic (22a) acid was collected. The ir spectrum (CHCl₃) of 22a exhibited a carbonyl adsorbtion at 1715 cm⁻¹.

The product obtained above (22a) may be converted to 16-phenyl-ω-tetranor-13,14 dihydro $PGF_{2\alpha}$ via the process of Example 16.

The product of this example may be converted to p-biphenyl esters of 16-phenyl-13,14-dihydro-ω-tetranorprostaglandins $E_2$, $A_2$, $F_{2\alpha}$, or $F_{2\beta}$ by the procedures outlined in Examples 28, 12, 14, 16, and 18.

EXAMPLE 23

9-Oxo-11α,15α-bis-(tetrahydropyran-2-yloxy)-16-phenyl-cis-5-ω-tetranor prostenoic acid (26a)

To a solution cooled to −10° under nitrogen of 880 mg (1.68 mmole) 9α-hydroxy-11α,15α-bis-(tetrahydropyran-2-yloxy)-16-phenyl-cis-5-ω-tetranor-prostenoic acid (22a) in 15 ml. reagent grade acetone was added dropwise 0.75 ml. (2 mmole) of Jones' reagent. After 20 minutes at −10°, 0.75 ml. 2-propanol was added and the reaction mixture was allowed to stir an additional 5 minutes at which time it was combined with 100 ml. ethyl acetate, washed with water (3 × 25 ml.), dried (MgSO₄) and concentrated to give 775 mg. of 9-oxo-11α,15α-bis-(tetrahydropyran-2-yloxy)-16-phenyl-cis-5-ω-tetranor prostenoic acid (26a). The ir spectrum (CHCl₃) had carbonyl adsorptions at 1710 and 1735 cm⁻¹.

The product of this example may be converted to p-biphenyl esters of 16-phenyl-13,14-dihydro-ω-tetranorprostaglandins $E_2$, $A_2$, $F_{2\alpha}$, and $F_{2\beta}$ by the procedures of Examples 29, 14, 16, and 18.

EXAMPLE 24

9-Oxo-11α,15α-dihydroxy-16-phenyl-cis-5-ω-tetranor prostenoic acid (27a)

A solution of 772 mg. 9-oxo-11α,15α-bis-(tetrahydropyran-2-yloxy)-16-phenyl-cis-5-ω-tetranor-prostenoic acid (26a) in 7.0 ml. of a 65:35 mixture of glacial acetic acid:water was stirred under nitrogen at 25° for 20 hours and then was concentrated by rotary evaporation. The resultant crude oil was purified by column chromatography on silica gel (Mallinckrodt CC-4 100–200 mesh) using ethyl acetate as eluent. After elution of less polar impurities, the oily 9-oxo-11α,15α-dihydroxy-16-phenyl-cis-5-ω-tetranor prostenoic acid (27a) weighing 361 mg. was collected. The ir spectrum (CHCl₃) exhibited carbonyl bands at 1710 and 1735 cm⁻¹.

EXAMPLE 25

9-Oxo-11α,15α-dihydroxy-16-phenyl-ω-tetranorprostanoic acid (28a)

A heterogeneous solution of 34 mg (0.89 mmole) 9-oxo-11α,15α-dihydroxy-16-phenyl-cis-5-trans-13-ω-tetranorprostadienoic acid (11a) and 13 mg of 5% palladium on carbon in 3 ml. absolute methanol was hydrogenated (1 atm) at 0° for 2 hours. The reaction mixture was filtered and evaporated to yield 30 mg of 9-oxo-11,15α-dihydroxy-16-phenyl-ω-tetranorprostanoic acid (28a). The ir (CHCl₃) of 28a exhibited carbonyl absorbtions at 1715 cm⁻¹ and 1735 cm⁻¹, a broad OH region and no trans double bond absorbtion.

EXAMPLE 26

9-oxo-11α,15α-dihydroxy-16-phenyl-trans-13-ω-tetranor prostenoic acid (29a)

A solution of 46 mg 9-oxo-11α,15α-dihydroxy-16-phenyl-cis-5-trans-13-ω-tetranor prostadienoic acid (11a) in 5 ml of dry ether was treated with 448 mg (3.6 mmole) dimethyl isopropyl chlorosilane and 360 mg (3.6 mmole) triethylamine at 25° for 48 hours. The reaction mixture was cooled to 0°, methanol was added and the resulting solution was washed with water (3 × 2 ml), dried (MgSo₄) and evaporated to a residue (67 mg). The crude residue was then taken up in 6 ml methanol and 30 mg of 50% Pd/C and the resultant slurry was hydrogenated for 4 hours at −22° (CCl₄/Dry Ice). After filtration through super cell and evaporation, the hydrogenated product was hydrolyzed in 2 ml of acetic acid-water (3:1) for 10 minutes, diluted with water (20 ml) and extracted with ethyl acetate (4 × 15 ml). The combined organic extracts were washed with water (2 × 10 ml), dried (MgSo₄) and evaporated to yield 44 mg of 9-oxo-11α,15α-dihydroxy-16-phenyl-trans-13-ω-tetranor prostenoic acid (29a).

EXAMPLE 27 p-Biphenyl 9-oxo-11α,15α-dihydroxy-16-phenyl-cis-5-trans-13-ω-tetranorprostadienoate A solution of 200 mg. (0.535 mmole) 9-oxo-11α,15α-dihydroxy-16-phenyl-cis-5-trans-13-ω-tetranor-prostadienoic acid (11a), 900 mg. (5.3 mmoles) p-phenylphenol, 7 ml. of 0.097 M dicyclohexylcarbodiimide in methylene chloride and 20 ml. methylene chloride was stirred overnight at room temperature. Concentration (in vacuo) and column chromatography on silica gel (Baker, 60–200 mesh) using chloroform then ethyl acetate as eluents yielded tetranorprostadienoate, m.p. 120°–121° (ether - pentane).

Using the above procedure the 15-substituted-ω-pentanor-prostaglandin p-biphenyl esters of this invention may be similarly obtained by substituting the appropriate 15-substituted-ω-pentanorprostaglandins for compound 11a of the above example.

EXAMPLE 28 p-Biphenyl 9α-hydroxy-11α,15α-bis-(tetrahydropyran-2-yloxy)-16-phenyl-cis-5-trans-13-ω-tetranorprostadienoate A solution of 9α-hydroxy-11α,15α-bis-(tetrahydropyran-2-yloxy)-16-phenyl-cis-5-trans-13-ω-tetranorprostadienoic acid (9a) (1 equivalent), p-phenylphenol (10 equivalents), and dicyclo-hexylcarbodiimide (1.25 equivalents) in methylene chloride are stirred overnight, concentrated (in vacuo) and purified by column chromatography to afford p-biphenyl 9α-hydroxy-11α,15α-bis-(tetrahydropyran-2-yloxy)-16-phenyl-cis-5-trans-13-ω-tetranorprostadienoate.

This material is converted to the p-biphenyl esters of 16-phenyl-ω-tetranorprostaglandin $E_2$, $F_{2\alpha}$, and $A_2$ by the procedures outlined in Examples 12, 14, 16, 18.

The product of this example may be reduced by the procedure of Example 25 to p-biphenyl 9α-hydroxy- 11α,15α-bis-(tetrahydropyranyl)-16-phenyl-ω-tetranor prostanoate or by the procedure of Example 26 to p-biphenyl 9α-hydroxy-11α,15α-bis-(tetrahydropyranyl)-16-phenyl-13-trans-ω-tetranor prostenoate. These materials are converted to the p-biphenyl esters of 16-phenyl-ω-tetranorprostaglandin $E_0$, $F_0\alpha$, $A_0$, and $F_0\beta$ or $E_1$, $F_{1\alpha}$, $A_1$, and $F_1\beta$ respectively by the procedures of Examples 12, 14, 16 and 18.

Using the above procedure the other 15-substituted-ω-pentanorprostaglandin p-biphenyl esters of this invention are similarly obtained by substituting the appropriate 11,15-bis-(tetrahydropyran-2-yloxy)-15-substituted-ω-pentanorprostaglandin for compound 9a of the above example.

EXAMPLE 29 p-Biphenyl 9-oxo-11α,15α-bis-(tetrahydropyran-2-yloxy)-16-phenyl-cis-5-trans-13-ω-tetranorprostadienoate A solution of 9-oxo-11α,15α-bis-(tetrahydropyran-2-yloxy)-16-phenyl-cis-5-trans-13-ω-tetranorprostadienoic acid (10a) (1 equivalent), p-phenylphenol (10 equivalents), and dicyclohexyl-carbodiimide (1.25 equivalents) in methylene chloride can be stirred overnight, concentrated (in vacuo), and purified by column chromatography to afford p-biphenyl 9-oxo-11α,15α-bis-(tetrahydropyran-2-yloxy)-16-phenyl-cis-5-trans-13-ω-tetranorprostadienoate.

This material may be converted to the p-biphenyl esters of 16-phenyl-ω-tetranorprostaglandin $E_2$ and $A_2$ by the procedures outlined in Examples 14 and 18.

Using the above procedures the other 15-substituted-pentanorprostaglandin p-biphenyl esters of this invention of the E and A series may be similarly obtained by substituting the appropriate 11,15-bis-(tetrahydropyran-2-yloxy)-15-substituted-ω-pentanorprostaglandin for compound 10a of the above example.

EXAMPLE 30 p-Phenylphenol Ester of 16-o-tolyl-ω-tetranorprostaglandin $E_2$

A solution of 77 mg. (0.20 mmole) 16-o-tolyl-ω-tetranorprostaglandin $E_2$, 340 mg. (2.0 mmole) p-phenylphenol, 2.58 ml. of 0.097 M dicyclohexylcarbodiimide in methylene chloride and 7.7 ml. methylene chloride was stirred overnight at room temperature. Concentration (in vacuo) and column chromatography on silica gel (Baker, 60–200 mesh) yielded 104 mg. (97%) of the p-phenylphenol ester of 16-o-tolyl-ω-tetranorprostaglandin $E_2$, m.p. 91°–91.5°, after crystallization from ether-pentane. The ir spectrum was in agreement with the assigned structure.

EXAMPLE 31

A solution of 12.4 g. (100 mmoles) dimethyl methylphosphonate (Aldrich) in 125 ml. dry tetrahydrofuran was cooled to −78° in a dry nitrogen atmosphere. To the stirred phosphonate solution was added 45 ml. of 2.37 M n-butyllithium in hexane solution dropwise over a period of 30 minutes at such a rate that the reaction temperature never rose above −65°. After an additional 5 minutes stirring at −78°, 6.6 g. (50.0 mmole) methyl 4-methoxybutyrate [prepared by the method of R. Huisgen and J. Reinertshafter, Am., 575, 197 (1952)] was added dropwise at a rate that kept the reaction temperature less than −70° (10 minutes). After 3 hours at −78° the reaction mixture was allowed to warm to ambient temperature, neutralized with 6 ml. acetic acid and rotary evaporated to a white gel. The gelatinous material was taken up in 25 ml. water, the aqueous phase extracted with 100 ml. portions of methylene chloride (3×), the combined organic extracts dried ($MgSO_4$), and concentrated (water aspirator) to a crude residue and distilled, b.p. 141°–145° (1.7–0.6 mm) to give 7.6 g. (68%) dimethyl 2-oxo-6-oxaheptylphosphonate.

Vapor phase chromatography analysis (a 5 foot × ¼ inch column containing 10% SE 30 on Chromosorb P, 80–100 mesh at 105° was employed) indicated a purity ≥ 99.9%. The nmr spectrum ($CDCl_3$) showed a doublet centered at 3.78 δ (J = 11.5 cps, 6H) for

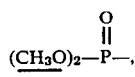

a triplet centered at 3.37 δ (2H) for

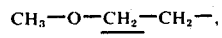

a singlet at 3.28 δ (3H) for

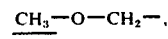

a doublet centered at 3.14 δ (J = 23 cps, 2H)

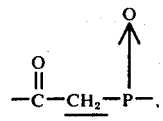

a triplet centered at 2.71 δ (2H) for

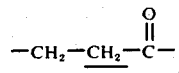

and a multiplet 1.57–2.10 δ (2H) for

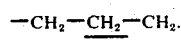

EXAMPLE 32

Dimethyl 2-oxo-6-oxaheptylphosphonate as prepared in Example I (1.68 g., 7.5 mmole), in 125 ml. anhydrous ether was treated with 2.5 ml. (5.9 mmole) 2.37M n-butyllithium in n-hexane in a dry nitrogen atmosphere at room temperature. After 5 minutes of stirring, an additional 225 ml. of anhydrous ether was added followed by 1.75 g. (5.0 mmole) 2-[3α-p-phenylbenzoyloxy-5α-hydroxy-2β-formylcyclopentan-1α-yl]acetic acid, γ-lactone in one portion. After 30 minutes the reaction mixture was quenched with 2.5 ml. glacial acetic acid, diluted with 200 ml. anhydrous ether, washed with 200 ml. 10% HCl (2 ×), 200 ml. saturated sodium bicarbonate solution (1 ×), 100 ml. water (1 ×), dried $MgSO_4$) and evaporated to yield 1.972 g. (88%) 2-[3α-p-phenylbenzoyloxy-5α- hydroxy-2β-(3-oxo-7-oxa-trans-1-octen-1-yl)cyclopent-1α-yl]acetic acid, γ-lactone as an oil.

The ir spectrum (CHCl₃) of the product exhibited adsorption bands at 1770 cm⁻¹ (strong), 1717 cm⁻¹ (strong), 1675 cm⁻¹ (medium) and 1630 cm⁻¹ (medium) attributable to the carbonyl groups. The uv spectrum had a $\lambda_{max} = 274$ mμ and $\epsilon_{max} = 21,380$ (ethanol solution). The nmr spectrum (CDCl₃) exhibited a multiplet at 7.23–8.18 δ (9H) for the p-biphenyl group, a doublet of doublets centered at 6.71 δ (1H, J = 7.16 cps) and a doublet centered at 6.27 δ (1H, J = 16 cps) for the olefinic protons, a triplet at 3.30 δ (2H) for

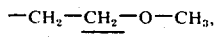

a singlet at 3.21 δ (3H) for

and multiplets at 4.90–5.50 δ (2H), 2.21–3.07 δ (8H) and 1.58–2.06 δ (2H) for the remainder of the protons.

EXAMPLE 33

To a solution of 1972 mg. (4.4 mmole) 2-[3α-p-phenylbenzoyloxy-5α-hydroxy-2β-(3-oxo-7-oxa-trans-1-octen-1-yl)cyclopent-1α-yl]acetic acid, γ-lactone as prepared in Example II in 15 ml. dry 1,2-dimethoxyethane in a dry nitrogen atmosphere at ambient temperature was added dropwise 4.0 ml. of a 0.5 M zinc borohydride solution. After stirring at room temperature for 1 hour, the reaction mixture was cooled to 0° and a saturated sodium bitartrate solution was added dropwise until hydrogen evolution ceased. The reaction mixture was allowed to stir for 5 minutes at which time 250 ml. dry methylene chloride was added. After drying (MgSO₄) and concentrating (water aspirator) the resultant semisolid was purified by column chromatography on silica gel (Baker "Analyzed" Reagent 60–200 mesh) using ether as eluent. After elution of less polar impurities, fractions containing 450 mg. 2-[3α-p-phenylbenzoyloxy-5α-hydroxy-2β-(3α-hydroxy-7-oxa-trans-1-octen-1-yl)cyclopent-1α-yl]acetic acid, γ-lactone, 294 mg. of 2-[3α-p-phenylbenzoyloxy-5α-hydroxy-2β-(3β-hydroxy-7-oxa-trans-1-octen-1-yl)cyclopent-1α-yl]acetic acid, γ-lactone, and 486 mg. of the two mixed were eluted.

The ir spectrum (CHCl₃) of the first of these two compounds had strong carbonyl absorptions at 1770 and 1715 cm⁻¹.

EXAMPLE 34

A heterogeneous mixture of 450 mg. (1.0 mmole) of 2-[3α-p-phenylbenzoyloxy-5α-hydroxy-2β-(3α-hydroxy-7-oxa-trans-1-octen-1-yl)cyclopent-1α-yl]acetic acid, γ-lactone as prepared in Example III, 4.5 ml. of absolute methanol and 140 mg. of finely powdered, anhydrous potassium carbonate was stirred at room temperature for 1 hour, then cooled to 0°. To the cooled solution was added 2.0 ml. (2.0 mmole) of 1.0N aqueous hydrochloric acid. After stirring at 0° an additional 10 minutes, 5 ml. of water was added with concomitant formation of methyl p-phenylbenzoate which was collected by filtration. The filtrate was saturated with solid sodium chloride, extracted with ethyl acetate (4 × 10 ml.), the combined organic extracts were washed with saturated sodium bicarbonate (10 ml.), dried (MgSO₄) and concentrated to give 204 mg. (76%) of viscous, oily 2-[3α,5α-dihydroxy-2β-(3α-hydroxy-7-oxa-trans-1-octen-1-yl)cyclopent-1α-yl]acetic acid, γ-lactone.

The ir spectrum (CHCl₃) exhibited a strong absorption at 1770 cm⁻¹ for the lactone carbonyl and medium absorption and medium absorption at 960 cm⁻¹ for the trans-double bond.

EXAMPLE 35

To a solution of 192 mg. (0.71 mmole) 2-[3α,5α-dihydroxy-2β-(3α-hydroxy-7-oxa-trans-1-octen-yl)cyclopent-1α-yl]acetic acid, γ-lactone as prepared in Example IV, in 5 ml. anhydrous methylene chloride and 1 ml. of 2,3-dihydropyran at 0° in a dry nitrogen atmosphere was added 5 mg. p-toluenesulfonic acid, monohydrate. After stirring for 15 minutes, the reaction mixture was combined with 100 ml. ether, the ether solution washed with saturated sodium bicarbonate (1 × 15 ml.) then saturated brine (1 × 15 ml.), dried (MgSO₄) and concentrated yield 310 mg. (100%) 2-[5α-hydroxy-3α-(tetrahydropyran-2-yloxy)-2β-(3α-[tetrahydropyran-2-yloxy]-7-oxa-trans-1-octen-1-yl)cyclopent-1α-yl]acetic acid γ-lactone.

The nmr spectrum (CDCl₃) exhibited a multiplet at 5.30–5.62 δ (2H) for the olefinic protons, a singlet at 3.34 δ (3H) for the methyl ether protons, and multiplets at 4.36–5.18 δ (4H), 3.22–4.24 δ (9H), and 1.18–2.92 δ (20H) for the remaining protons.

EXAMPLE 36

A solution of 310 mg. (0.71 mmole) 2-[5α-hydroxy-3α-(tetrahydropyran-2-yloxy)-2β-3α-[tetrahydropyran-2-yloxy]-7-oxa-trans-1-yl)cyclopent-1α-yl, acetic acid, γ-lactone as prepared in Example V in 5 ml. dry toluene was cooled to −78° in a dry nitrogen atmosphere. To this cooled solution was added 1.5 ml. of 20% diisobutylaluminum hydride in n-hexane dropwise at such a rate so that the internal temperature never rose about −65° (15 minutes). After an additional 45 minutes of stirring at −78°, anhydrous methanol was added until gas evolution ceased and the reaction mixture was allowed to warm to room temperature. The reaction mixture was combined with 100 ml. ether, washed with 50% sodium potassium tartrate solution (4 × 20 ml.), dried (MgSO₄) and concentrated to yield 290 mg. (93%) 2-[5α-hydroxy-3α-(tetrahydropyran-2-yloxy)-2β-(3α-[tetrahydropyran-2-yloxy]-7-oxa-trans-1-octen-1-yl)cyclopent-1-yl]acetaldehyde, γ-hemiacetal.

EXAMPLE 37

To a solution of 870 mg. (2.0 mmole) (4-carbohydroxy-n-butyl) triphenylphosphonium bromide in a dry nitrogen atmosphere in 5.0 ml dry dimethyl sulfoxide was added 2.0 ml. (4.4 mmole) of a 2.2 M solution of sodium methylsulfinylmethide in dimethyl sulfoxide. To this red ylide solution was added dropwise a solution of 290 mg. (0.66 mmole) 2-[5α-hydroxy-3α-(tetrahydropyran-2-yloxy)-2β-(3α-[tetrahydropyran-2-yloxy]-7-oxa-trans-1-octen-1-yl)cyclopent-1α-yl]acetaldehyde, γ-hemiacetal as prepared in Example VI in 3.0 ml. dry dimethyl sulfoxide over a period of 20 minutes. After an additional 2 hours stirring at room temperature, the reaction mixture was poured onto ice water. The basic aqueous solution was washed twice with ethyl acetate (20 ml.) and acidified to pH ~ 3 with 10% aqueous hydrochloric acid. The acidic solution was extracted with ethyl acetate (3 × 20 ml.) and the combined organic extracts washed once with water (10 ml.), dried (MgSO$_4$) and evaporated to a solid residue weighing 784 mg. This solid residue was triturated with ethyl acetate and filtered. The filtrate was purified by column chromatography on silica gel (Baker "Analyzed" Reagent 60–200 mesh) using ethyl acetate as eluent. After removal of high R$_f$ impurities, 225 mg. (66%) of 9α-hydroxy-11α,15α-bis-(tetrahydropyran-2-yloxy)-19-oxa-cis-5-trans-13-prostadienoic acid was collected.

The nmr spectrum (CDCl$_3$) exhibited a multiplet (variable at 5.84–6.38δ (2H) for the —OH protons, a multiplet at 5.27–5.68δ (4H) for the olefinic protons, a multiplet at 4.52–4.84δ (2H) for the acetal protons, a singlet at 3.34δ (3H) for the methyl ether protons and multiplets at 3.25–4.35δ (9H) and 1.20–2.72 δ (28H) for the remaining protons.

This is suitable for many of the p-biphenyl esters of 19-oxa prostaglandins such as 19-oxaprostaglandin F$_{o2}$, F$_{12}$, F$_2$ $_\alpha$, E$_2$, E$_1$, E$_o$, A$_2$, A, and A$_o$. The transformation required are those of example 30.

EXAMPLE 38

To a solution cooled to −10° under nitrogen of 190 mg. (0.356 mmole) 9α-hydroxy-11α,15α-bis-(tetrahydropyran-2-yloxy)-19-oxa-cis-5-trans-13-prostadienoic acid as prepared in Example VII, in 5 ml. reagent grade acetone was added dropwise 0.143 ml. (0.356 mmole) of Jones' reagent. After 20 minutes at −10°, 0.140 ml. 2-propanol was added and the reaction mixture was allowed to stir an additional 5 minutes at which time it was combined with 40 ml. ethyl acetate, washed with water (3 × 5 ml.), dried (MgSO$_4$) and concentrated to give 174 mg. of 9-oxo-11α,15α-bis-(tetrahydropyran-2-loxy)-19-oxa-cis-5-trans-13-prostadienoic acid.

This product is transformed into its p-biphenyl ester via the procedure of example 28.

EXAMPLE 39

A solution of 174 mg. (0.334 mmole) 9-oxo-11α,15α-bis-tetrahydropyran-2-yloxy)-19-oxa-cis-5-trans-13-prostadienoic acid as prepared in Example VIII and 3.0 ml. of a 65:35 mixture of glacial acetic acid:water was stirred under nitrogen at 40° for 5 hours and then was concentrated by rotary evaporation. The resultant crude oil was purified by column chromatography on silica gel (Mallinckrodt CC-4 100–200 mesh) using ethyl acetate as eluent. After elution of less polar impurities the semisolid 9-oxo-11α,15α-dihydroxy-19-oxa-cis-5-trans-13-prostadienoic acid weighing 33 mg. was collected. This product is 19-oxaprostaglandin E$_2$, m.p. 58°–9° (ethyl acetate, cyclohexane).

Analysis: Calc'd for C, 64.39; H, 8.53.
Found C, 64.30; H, 8.28.
$[\alpha]_D^{25} = -71.2°$ (C = 1.0, methanol)

The ir spectrum (CHCl$_3$) of the product exhibited a strong adsorption at 1715 cm$^{-1}$ for the carbonyls and a medium band at 965 cm$^{-1}$ for the trans double bond. The uv spectrum in methanol with added potassium hydroxide solution exhibited a $\lambda_{max}$ 278 mμ and an $\epsilon_{max}$ 28,000.

If the corresponding 19-oxaprostaglandin A$_2$ is desired, the above 19-oxoprostaglandin E$_2$ may be treated with formic acid, and the product then purified by column chromatography.

These products are transformed into their p-biphenyl esters by the procedure of example 27.

EXAMPLE 40

A solution of 52 mg. (0.10 mmole) 9α-hydroxy-11α,15α-bis-(tetrahydropyran-2-yloxy)-19-oxa-cis-5-trans-13-prostadienoic acid as prepared in Example VII, in 3.0 ml. of a 65:35 mixture of glacial acetic acid:-water was stirred under nitrogen at 40° for 5 hours then was concentrated by rotary evaporation. The resultant crude oil was purified on silica gel (Mallinckrodt CC-4 100–200 mesh) using ethyl then methanol as eluents. After elution of less polar impurities the oily 9α,11α,15α-trihydroxy-cis-5-trans-13-prostadienoic acid weighing 15 mg. was collected. This product is 19-oxoprostaglandin F$_{2\alpha}$.

The product is transformed into its p-biphenyl ester by the procedure of example 27.

EXAMPLE 41 p-Phenylphenol Ester of 13,14-dihydro-15methyl-16-phenyl-ω-tetranorprostaglandin E$_2$ A solution of 150 mg. (0.388 mmole) 13,14-dihydro-15-methyl-16-phenyl-ω-tetranorprostaglandin E$_2$, 645 mg. (3.8 mmole) p-phenylphenol, 4 ml. of 0.1 M dicyclohexylcarbodiimide in methylene chloride and 12 ml. methylene chloride was stirred overnight at room temperature. Concentration (in vacuo) and column chromatography on silica gel (Baker, 60–200 mesh) yielded 24 mg. of the p-phenylphenol ester of 13,14-dihydro-15-methyl-16-phenyl-ω-tetranorprostaglandin E$_2$, m.p. 74°–7°, after crystallization from ether-pentane. The ir and mass spec spectra were in agreement with the assigned structure. Separation of the 15 R and 15 S epimers was achieved by liquid chromatography.

EXAMPLE 42 p-Phenylphenol Ester of 17-phenyl-ω-trisnorprostaglandin E$_2$

A solution of 50 mg. (0.13 mmole) 17-phenyl-ω-trisnorprostaglandin E$_2$, 220 mg. (1.30 mmole) p-phenylphenol, 1.79 ml. of 0.10 M dicyclohexylcarbodiimide in methylene chloride and 5 ml. methylene chloride was stirred overnight at room temperature. Concentration (in vacuo) and column chromatography on silica gel (Baker, 60–200 mesh) yielded 51 mg. (73.6%) of the p-phenylphenol ester of 17-phenyl- -ω-trisnorprostaglandin E$_2$, m.p. 114.5°–115.5°, after crystallization from methylene chloride-hexane. The IR spectrum was in agreement with the assigned structure.

EXAMPLE 43 p-Phenylphenol Ester of 16-β-napthyl-ω-tetranorprostaglandin E$_2$

A solution of 200 mg. (.474 mmole) 16-β-napthyl-ω-tetranorprostaglandin E$_2$, 900 mg. (5.3 mmole) p-phenylphenol, 7 ml. of 0.097 M dicyclohexylcarbodiimide in methylene chloride and 20 ml. methylene chloride was stirred overnight at room temperature. Concentration (in vacuo) and column chromatography on silica gel (Baker, 60–200 mesh) yielded 72 mg. of the p-phenylphenol ester of 16-β-naphthyl-ω-tetranorprostaglandin $E_2$, m.p. 79°–82°, after crystallization from ether-pentane. The IR and mass spec, spectra were in agreement with the assigned structure.

EXAMPLE 44 p-Phenylphenol Ester of 13,14-dihydro-15-methyl-16-phenyl-ω-tetranorprostaglandin $E_2$ A solution of 150 mg. (0.388 mmole) 13,14-dihydro-15-methyl-16-phenyl-ω-tetranorprostaglandin $E_2$, 645 mg. (3.8 mmole) p-phenylphenol, 4 ml. of 0.1 M dicyclohexylcarbodiimide in methylene chloride and 12 ml. methylene chloride was stirred overnight at room temperature. Concentration (in vacuo) and column chromatography on silica gel (Baker, 60–200 mesh) yielded 24 mg. of the p-phenylphenol ester of 13,14-dihydro-15-methyl-16-phenyl-ω-tetranorprostaglandin $E_2$, m.p. 74°–7°, after crystallization from ether-pentane. The ir and mass spec spectra were in agreement with the assigned structure. Separation of the 15 R and 15 S epimers was achieved by liquid chromatography.

EXAMPLE 45 p-Phenylphenol ester of 16-α-thienyl-ω-tetranorprostaglandin $E_2$

A solution of 246 mg. (.65 mmole) 16-α-thienyl-ω-tetranorprostaglandin $E_2$, 680 mg. (4 mmole) p-phenylphenol, 412 mg. (1 mmole) dicyclohexylcarbodiimide in methylene chloride and 15 ml. methylene chloride was stirred overnight at room temperature. Concentration (in vacuo) and column chromatography on silica gel (Baker, 60–200 mesh) yielded 60 mg. of the p-phenylphenol ester of 16-α-thienyl-ω-tetranorprostaglandin $E_2$, m.p. 115°–117°, after crystallization from ether-pentane.

In the same manner the p-phenylphenol ester of 16-β-thienyl-107-tetranorprostaglandin $E_2$, m.p. 126°–8°, was prepared.

EXAMPLE 46 p-Phenylphenol Ester of 19-oxa-prostaglandin $E_2$

A solution of 167 mg. (0.47 mmole) 19-oxa-prostaglandin $E_2$, 800 mg. (4.7 mmole) p-phenylphenol, 6 ml. of 0.1 M dicyclohexylcarbodiimide in methylene chloride and 20 ml. methylene chloride was stirred overnight at room temperature. Concentration (in vacuo) and column chromatography on silica gel (Baker, 60–200 mesh) yielded 53 mg. (23%) of the p-phenylphenol ester of 19-oxa-prostaglandin $E_2$, m.p. 87°–87.5°, after crystallization from ether-pentane. The ir spectrum was in agreement with the assigned structure.

EXAMPLE 47 p-Phenylphenol Ester of 19-oxa-prostaglandin $F_{2\alpha}$:

A solution of 180 mg. (0.55 mmole) 19-oxa-prostaglandin $F_{2\alpha}$, 940 mg. (5.5 mmole) p-phenylphenol, 7 ml. of 0.97 M dicyclohexylcarbodiimide in methylene chloride and 20 ml. methylene chloride was stirred overnight at room temperature. Concentration (in vacuo) and column chromatography on silica gel (Baker, 60–200 mesh) yielded 156 mg. (56%) of the p-phenylphenol ester of 19-oxa-prostaglandin $F_{2\alpha}$, m.p. 104°–5°, after crystallization from ether. The ir spectrum was in agreement with the assigned structure.

Biphenyl 9,15-Dioxo-11α-Hydroxy-17-phenyl-cis-5-trans-13-ω-trisnorprostadienoate A heterogeneous solution of 538 mg (1.0 mmole) biphenyl 9-oxo-11α,15β-dihydroxy-17-phenyl-cis-5-trans-13ω-trisnorprostadienoate, 5 g $MnO_2$ and 50 ml dry methylene chloride is stirred overnight at room temperature, filtered, and evaporated to yield biphenyl 9,15-dioxo-11α-hydroxy-17-phenyl-cis-5-trans-13-ω-trisnorprostadienoate.

Biphenyl 9α,11α,15α-Trihydroxy-17-phenyl-cis-5-trans-13-ω-trisnorprostadienoate A chilled solution of 3 g sodiumborohydride in 350 ml. absolute methanol is added to 538 mg (1.0 mmole) biphenyl 9,15-dioxo-11-hydroxy-17-phenyl-cis-5-trans-13-ω-trisnorprostadienoate in 100 ml. absolute methanol. After stirring at 0° for 20 minutes then 1 hr at room temperature the reaction mixture is cooled, water is added (20 ml) and the reaction mixture is stripped to a residue. The residue is covered with 100 ml. ethyl acetate and acidified (pH-3) with 10% HCl. The aqueous portion if further extracted with ethyl acetate (4 × 50 ml) and the combined organic is washed with water dried ($NA_2SO_4$) and evaporated to yield a mixture of biphenyl 9α,11α,15α-, 9α,11α,15β-, 9β,11α,15α-, and 9β,11α,15β-Trihydroxy-17-phenyl-cis-5-trans-13-ω-trisnorprostadienoates. These four isomers are separated by column and liquid chromatography.

EXAMPLE 48 p-Phenylphenol Ester of 15-epi-16-β-naphthyl-ω-tetranorprostaglandin $E_2$

A solution of 200 mg. (.474 mmole) 15-epi-16-β-napthyl-ω-tetranorprostaglandin $E_2$, 900 mg. (5.3 mmole) p-phenylphenol, 7 ml. of 0.097 M dicyclohexylcarbodiimide in methylene chloride and 20 ml. methylene chloride was stirred overnight at room temperature. Concentration (in vacuo) and column chromatography on silica gel (Baker, 60–200 mesh) yielded 50 mg. of the p-phenylphenol ester of 15-epi-16-β-napthyl-tetranorprostaglandin $E_2$, m.p. 101°–3°, after crystallization from ether-pentane.

In the same manner, the p-phenylphenol ester of 16-β-naphthyl-ω-tetranorprostaglandin $E_2$, m.p. 79°–82° was prepared.

EXAMPLE 49 p-Phenylphenol Ester of 16-phenyl-13,14-dihydro-ω-tetranor-prostaglandin $E_2$ A solution of 120 mg. (0.32 mmole) 16-phenyl-13,14-dihydro-ω-tetranorprostaglandin $E_2$, 545 mg. (3.2 mmole) p-phenylphenol, 4.1 ml. of 0.097 M dicyclohexylcarbodiimide in methylene chloride and 18 ml. methylene chloride was stirred overnight at room temperature. Concentration (in vacuo) and column chromatography on silica gel (Baker, 60–200 mesh) yielded 75 mg. (44%) of the p-phenylphenol ester of 16-phenyl-13,14-dihydro-ω-tetranor-prostaglandin $E_2$, m.p. 90.5–92°, after crystallization from ether-pentane. The ir, nmr and mass spec were in agreement with the assigned structure.

Analysis: Calc'd. for: $C_{38}H_{38}O_5$ C, 77.53; H, 7.27. Found: C, 77.23; H, 7.31.

EXAMPLE 50 p-Phenylphenol ester of 16-α-thienyl-ω-tetranorprostaglandin $E_2$

A solution of 246 mg. (.65 mmole) 16-α-thienyl-ω-tetranorprostaglandin $E_2$, 680 mg. (4 mmole) p-phenylphenol, 412 mg. (1 mmole) dicyclohexylcarbodiimide in methylene chloride and 15 ml. methylene chloride was stirred overnight at room temperature. Concentration (in vacuo) and column chromatography on silica gel (Baker, 60–200 mesh) yielded 60 mg. of the p-phenylphenol ester of of 16-α-thienyl-ω-tetranorprostaglandin $E_2$, m.p. 115°–117°, after crystallization from ether-pentane.

In the same manner, the p-phenylphenol ester of 16-β-thienyl-ω-tetranorprostaglandin $E_2$, m.p. 126°–8°, was prepared.

EXAMPLE 51 p-Phenylphenol Ester of 17-α-Furyl -trisnorprostaglandin $F_{2\ \alpha}$ :

A solution of 177 mg. (0.35 mmole) 17-α-furyl-ω-trisnorprostaglandin $F_{2\ \alpha}$, 668 mg, (0.39 mmole) p-phenylphenol, 4.95 ml. of M m dicyclohexylcarbodiimide in methylene chloride and 15 ml. methylene chloride was stirred overnight at room temperature. Concentration (in vacuo) and column chromatography on silica gel (Baker, 60–200 mesh) yielded 28 mg. of the p-phenylphenol ester of 17-α-furyl-ω-trisnorprostaglandin $F_{2\alpha}$ m.p. 122°–24°, after crystallization from ether pentane.

EXAMPLE 52 p-Phenylphenol Ester of 16-β-thienyl-ω-tetranorprostaglandin $E_2$

A solution of 130 mg. (0.344 mmole) 16-β-thienyl-ω-tetra-norprostaglandin, 653 mg. (0.38 mmole) p-phenylphenol, 4.85 ml. of 0.1 M dicyclohexylcarbodiimide in methylene chloride and 15 ml. methylene chloride was stirred overnight at room temperature. Concentration (in vacuo) and column chromatography on silica gel (Baker, 60–200 mesh) yielded 18 mg. of the p-phenylphenol ester of 16-β-thienyl-ω-tetranorprostaglandin, m.p. 126°–28°, after crystallization from ether-pentane. The IR, mass spec, NMR, UR spectra were in agreement with the assigned structure.

EXAMPLE 53 p-Phenylphenol Ester of 13,14-dihydro-15-phenyl-ω-pentanor-prostaglandin $E_2$ A solution of 146 mg. (.405 mmole) 13,14-dihydro-15-phenyl-ω-pentanorprostaglandin $E_2$, 770 mg. (4.53 mmole) p-phenylphenol, 6 ml. of 0.097 M dicyclohexylcarbodiimide in methylene chloride and 15 ml. methylene chloride was stirred overnight at room temperature. Concentration (in vacuo) and column chromatography on silica gel (Baker, 60–200 mesh) yielded 76 mg. of the p-phenylphenol ester of 13,14-dihydro-15-phenyl-ω-pentanor-prostaglandin $E_2$, m.p. 87°–90°, after crystallization from ether-pentane. The IR and mass spec spectra were in agreement with the assigned structure. The 15 (R) and 15 (S) epimers were separated by thin layer chromatography.

EXAMPLE 54 p-Phenylphenol Ester of 13,14-dihydro-16-phenyl-ω-tetranor-prostaglandin $E_1$ A solution of 36 mg. (0.096 mmole) 13,14-dihydro-16-phenyl-ω-tetranorprostaglandin $E_1$, 164 mg. (0.96 mmole) p-phenylphenol, 1.5 ml. of 0.097 M dicyclohexylcarbodiimide in methylene chloride and 5 ml. methylene chloride was stirred overnight at room temperature. Concentration (in vacuo) and column chromatography on silica gel (Baker, 60–200 mesh) yielded 10 mg. of the p-phenylphenol ester of 13,14-dihydro-16-phenyl-ω-tetranorprostaglandin $E_1$, m.p. 96°–100°, after crystallization from ether-pentane.

EXAMPLE 55 p-Phenylphenol Ester of 16-phenyl-ω-tetranorprostaglandin $E_1$

A solution of 44 mg. (0.12 mmole) 16-phenyl-ω-tetranorprostaglandin $E_1$, 204 mg. (1.2 mmole) p-phenylphenol, 2.6 ml. of 0.097 M dicyclohexylcarbodiimide in methylene chloride and 5 ml. methylene chloride was stirred overnight at room temperature. Concentration (in vacuo) and column chromatography on silica gel (Baker, 60–200 mesh) yielded the p-phenylphenol ester of 16-phenyl-ω-tetranorprostaglandin $E_1$, m.p. 95°–6°, after crystallization from ether-pentane.

EXAMPLE 56 p-Phenylphenol Ester of 16-p-methoxyphenyl-ω-tetranorprostaglandin

A solution of 76 mg. (0.19 mmole) 16-p-methoxyphenyl-ω-tetranorprostaglandin $E_2$, 322 mg. (1.9 mmole) p-phenylphenol, 2.27 ml. of 0.09 M dicyclohexylcarbodiimide in methylene chloride and 10 ml. methylene chloride was stirred overnight at room temperature. Concentration (in vacuo) and column chromatography on silica gel (Baker, 60–200 mesh) yielded 26 mg. (25%) of the p-phenylphenol ester of 16-p-methoxyphenyl-ω-tetranorprostaglandin $E_2$, m.p. 108°–110°, after crystallization from ether-pentane.

EXAMPLE 57 p-Phenylphenol Ester of 16-p-tolyl-ω-tetranorprostaglandin $E_2$

A solution of 200 mg. (0.52 mmole) 16-p-tolyl-ω-tetranor-prostaglandin $E_2$, 875 mg. (5.2 mmole) p-phenylphenol, 6.2 ml. of 0.097 M dicyclohexylcarbodiimide in methylene chloride and 20 ml. methylene chloride was stirred overnight at room temperature. Concentration (in vacuo) and column chromatography on silica gel (Baker, 60–200 mesh) yielded 75 mg. (27%) of the p-phenylphenol ester of 16-p-tolyl-ω-tetranorprostaglandin $E_2$, m.p. 104°, after crystallization from ether-pentane.

EXAMPLE 58 p-Phenylphenol Ester of 17-phenyl-ω-trisnorprostaglandin $F_{2\alpha}$:

A solution of 50 mg. (0.13 mmole) 17-phenyl-ω-tris-nor-prostaglandin $F_{2\ \alpha}$, 220 mg. (1.30 mmole) p-phenylphenol, 1.79 ml. of 0.10 M dicyclohexylcarbodiimide in methylene chloride and 5.0 ml. methylene chloride was stirred overnight at room temperature. Concentration (in vacuo) and column chromatography on silica gel (Baker, 60–200 mesh) yielded 63 mg.

(90.5%) of the p-phenylphenol ester of 17-phenyl-ω-trisnorprostaglandin F₂ α , m.p. 116°–117°, after crystallization from methylene chloride-hexane. The IR spectrum was in agreement with the assigned structure.

EXAMPLE 59 p-Phenylphenol Ester of 16-phenyl-ω-tetranorprostaglandin E₂

A solution of 200 mg. (0.535 mmole) 16-phenyl-ω-tetranor-prostaglandin E₂, 900 mg. (5.3 mmole) p-phenylphenol, 7 ml. of 0.097 M dicyclohexylcarbodiimide in methylene chloride and 20 ml. methylene chloride was stirred overnight at room temperature. Concentration (in vacuo) and column chromatography on silica gel (Baker, 60–200 mesh) yielded 185 mg. (66.5%) of the p-phenylphenol ester of 16-phenyl-ω-tetranorprostaglandin E₂, m.p. 120°–1°, after crystallization from ether-pentane. The ir, mass spec, and U$^V$ spectra were in agreement with the assigned structure.

Prostaglandin parabiphenyl esters prepared according to the previous examples:

|  | Melting point°C |
|---|---|
| 16-phenyl-ω-tetranor prostaglandin E₂ | 120–121 |
| 13,14-dihydro 16-phenyl-ω-tetranor PGE₂ | 108– |
| 16-phenyl-ω-tetranor PGE₁ | 95–96 |
| 16-phenyl-ω-tetranor PGE₀ | 96–100 |
| 17-phenyl-ω-tetranor PGE₂ | 114.5–115.5 |
| 17-phenyl-ω-trisnor PGF₂α | 116–117 |
| 17α-furyl-ω-trisnor PGF₂α | 122–124 |
| 16β-naphthyl-ω-tetranor PGE₂ | 79–82 |
| 16o-tolyl-ω-tetranor PGE₂ | 91–91.5 |
| 16p-tolyl-ω-tetranor PGE₂ | 104 |
| 16-paramethoxyphenyl-ω-tetranor PGE₂ | 108–110 |
| 16α-thienyl-ω-tetranor PGE₂ | 115–117 |
| 16β-thienyl-ω-tetranor PGE₂ | 126–128 |
| 15-phenyl 13,14-dihydro-ω-pentanor PGE₂ | 87–90 |
| 15-methyl 16-phenyl 13,14-dihydro-ω-tetranor PGE₂ | 74–77 |
| 19-oxa PGE₂ | 87–87.5 |
| 19-oxa PGF₂α | 104–105 |
| 20-oxa-ω-homo PGE₂ | 72–73 |
| 17-oxa PGF₂α | 93–94.5 |
| 13,14-dihydro 15-epi 16-phenyl-ω-tetranor PGE₂ | 111.5–113.5 |
| 13,14 dihydro 16-phenyl-ω-tetranor PGF₂β | 129–131 |
| 16-parabiphenyl-ω-tetranor PGE₂ | 107–109 |
| 15-epi 16β-naphthyl-ω-tetranor PGE₂ | 101–103 |
| 20-oxa-ω-homo PGF₂α | 104–105 |
| 16α-thienyl-ω-tetranor PGE₁ | 120–121 |
| 16 phenyl-ω-tetranor PGF₂α | 117–119 |
| 16-phenyl-13,14-dihydro-ω-tetranor PGF₂α | 79–81 |
| 18-phenyl-ω-bisnor PGE₂ | 83.5–84.5 |
| 18-phenyl-ω-bisnor PGF₂α | 98.5–99.5 |

What is claimed is:

1. The parabiphenyl esters of ω-pentanorprostaglandins having at the C₁₅ position one hydrogen or lower alkyl group and one substituent of the structure:

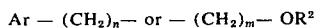

wherein
n is an integer from 0 to 5, with the proviso that when n is zero, said prostaglandin is a 13,14-dihydroprostaglandin;
m is an integer from 1 to 4;
R² is lower alkyl,
and Ar is α- or β-furyl; α- or β-thienyl; α- or β-naphthyl; phenyl; 3,4-dimethoxy phenyl; 3,4-methylenedioxyphenyl; 3,4,5-trimethoxyphenyl or monosubstituted phenyl wherein said substituent is chloro, trifluoromethyl, phenyl, lower alkyl or lower alkoxy.

2. A compound of the structure:

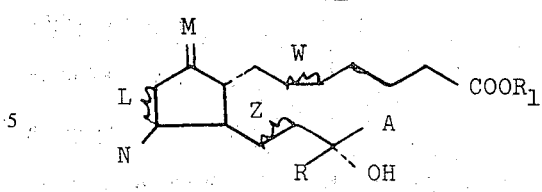

wherein
A is:

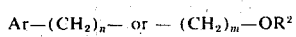

wherein
n is an integer from 0 to 5,
m is an integer from 2 to 3,
R² is lower alkyl,
Ar is α- or β-furyl; α- or β-thienyl; α- or β-naphthyl; phenyl; 3,4-dimethoxy phenyl; 3,4-methylenedioxyphenyl; 3,4,5-trimethoxyphenyl or monosubstituted phenyl wherein said substituent is chloro, trifluoromethyl, phenyl, lower alkyl or lower alkoxy,
R₁ is parabiphenyl;
R is hydrogen or lower alkyl;
W and L are each a single bond or cis double bond;
Z is a single bond or trans double bond; with the proviso that when n is zero, Z is a single bond;
M is keto,

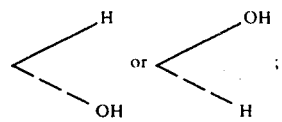

N is hydrogen or α-hydroxyl;
and wherein
L, M and N are so selected as to complete the structure of a prostaglandin of the A, E or F series.

3. The compounds of claim 1 wherein said C₁₅ substituent is Ar — (CH₂)ₙ—.

4. The compounds of claim 1 wherein said C₁₅ substituent is: (CH₂)ₘ—OR².

5. The compounds of claim 3 wherein said prostaglandin is of the E series.

6. The compounds of claim 3 wherein said prostaglandin is of the F series.

7. The compounds of claim 3 wherein said prostaglandin is of the A series.

8. The compounds of claim 4 wherein said prostaglandin is of the E series.

9. The compounds of claim 4 wherein said prostaglandin is of the F series.

10. The compounds of claim 4 wherein said prostaglandin is of the A series.

11. The compound of claim 5 wherein Ar is phenyl, n is 1 and said prostaglandin is PGE₂.

12. The compound of claim 5 wherein Ar is phenyl, n is 1 and said prostaglandin is 13,14 dihydro PGE₂.

13. The compound of claim 5 wherein Ar is phenyl, n is 1 and said prostaglandin is PGE₁.

14. The compound of claim 5 wherein Ar is phenyl, n is 1 of said prostaglandin is PGE₀.

15. The compound of claim 5 wherein Ar is phenyl, n is 2 and said prostaglandin is PGE₂.

16. The compound of claim 6 wherein Ar is phenyl, n is 2 and said prostaglandin is PGF₂α.

17. The compound of claim 5 wherein Ar is phenyl, n is 2 and said prostaglandin is PGE₂.

18. The compound of claim 5 wherein Ar is β-naphthyl, $n$ is 1 and said prostaglandin is $PGE_2$.

19. The compound of claim 5 wherein Ar is o-tolyl, $n$ is 1 and said prostaglandin is $PGE_2$.

20. The compound of claim 5 wherein Ar is p-tolyl, $n$ is 1 and said prostaglandin is $PGE_2$.

21. The compound of claim 5 wherein Ar is p-methoxyphenyl, $n$ is 1 and said prostaglandin is $PGE_2$.

22. The compound of claim 5 wherein Ar is α-thienyl, $n$ is 1 and said prostaglandin is $PGE_2$.

23. The compound of claim 5 wherein Ar is β-thienyl, $n$ is 1 and said prostaglandin is $PGE_2$.

24. The compound of claim 6 wherein Ar is α-thienyl, $n$ is 2 and said prostaglandin is $PGF_{2\alpha}$.

25. The compound of claim 6 wherein Ar is α-furyl, $n$ is 2 and said prostaglandin is $PGF_{2\alpha}$.

26. The compound of claim 5 wherein Ar is phenyl, $n$ is 0 and said prostaglandin is 13,14 dihydro $PGE_2$.

27. The compound of claim 5 wherein Ar is phenyl, $n$ is 1 and said prostaglandin is 15 methyl 13,14 dihydro $PGE_2$.

28. The compound of claim 8 wherein $m$ is 3, $R^2$ is methyl and said prostaglandin is $PGE_2$.

29. The compound of claim 9 wherein $m$ is 3, $R^2$ is methyl and said prostaglandin is $PGF_{2\alpha}$.

30. The compound of claim 8 wherein $m$ is 4, $R^2$ is methyl and said prostaglandin is $PGE_2$.

31. The compound of claim 9 wherein $m$ is 4, $R^2$ is methyl and said prostaglandin is $PGF_{2\alpha}$.

32. The compound of claim 9 wherein $m$ is 1, R is n-propyl and said prostaglandin is $PGF_{2\alpha}$.

33. The compound of claim 5 wherein $n$ is 1, Ar is phenyl and said prostaglandin is 15 epi 13,14 dihydro $PGE_2$.

34. The compound of claim 6 wherein $n$ is 1, Ar is phenyl and said prostaglandin is $PGF_{2\alpha}$.

35. The compound of claim 6 wherein $n$ is 1, Ar is phenyl and said prostaglandin is 13,14 dihydro $PGF_{2\beta}$.

36. The compound of claim 5 wherein $n$ is 1, Ar is p-biphenyl and said prostaglandin is $PGE_2$.

37. The compound of claim 5 wherein $n$ is 1, Ar is β-naphthyl and said prostaglandin is 15 epi-ω-tetranor $PGE_2$.

* * * * *